(12) United States Patent
Cosnier

(10) Patent No.: US 6,197,881 B1
(45) Date of Patent: Mar. 6, 2001

(54) ELECTRICALLY CONDUCTIVE COPOLYMERS AND THEIR PREPARATION

(75) Inventor: Serge Cosnier, Grenoble (FR)

(73) Assignee: Biopixel Ltd., Beer Sheba (IL)

( * ) Notice: Subject to any disclaimer, the term of this patent is extended or adjusted under 35 U.S.C. 154(b) by 0 days.

(21) Appl. No.: 09/376,692

(22) Filed: Aug. 18, 1999

(51) Int. Cl.$^7$ .......................... C08G 63/48; C08G 63/91; C12N 11/02; C12N 11/06; C12N 11/08
(52) U.S. Cl. ...................... 525/54.1; 525/54.2; 525/54.3; 435/177; 435/180; 435/181; 436/528; 436/531; 436/532; 530/391.1; 530/391.3; 530/391.5; 530/391.9; 530/815; 530/816
(58) Field of Search .................................. 524/54.1, 54.2, 524/54.3; 435/177, 180, 181; 436/528, 531, 532; 530/391.1, 391.3, 391.5, 391.9, 815, 816

(56) References Cited

U.S. PATENT DOCUMENTS 5,837,859   11/1998   Teoule et al. ...................... 536/25.3

FOREIGN PATENT DOCUMENTS

| 0 691 978 | 1/1996 | (EP) . |
| WO 94/22889 | 10/1994 | (WO) . |
| WO 99/24645 | 5/1999 | (WO) . |

OTHER PUBLICATIONS

S, Cosnier, et al., "Alkylammonium and pyridinium group-containing polypyrroles, a new class of electronically conducting anoin–exchange polymers", *J. Electroanal. Chem.*, 271 (1989), pp. 69–81.
N. C. Foulds and C. R. Lowe, "Enzyme entrapment in electrically conducting polymers", *J. Chem. Soc., Faraday Trans. 1*, 82 (1986), pp. 1259–1264.
D. Pantano and W. G. Kuhr, "Dehydrogenase–modified carbon fiber microelectrodes for the measurement of neurotransmitter dynamics. 2. Covalent modification utilizing avidin–biotin technology", Anal. Chem. 65 (1993), pp. 623–630.
S. Lee et al., "Enzyme–modified Langmuir–Blodgett membranes in glucose electrodes based on avidin biotin interaction", *Sensors and Actuators B*, 12 (1993), pp. 153–158.
J. Anazai et al., "Elimination of ascorbate interference of glucose biosensors by use of enzyme multilayers composed of avidin and biotin–labeled glucose oxidase and ascorbate oxidase", *Denki Kagaku*, 63 (1995), pp. 1141–1142.
W. Schuhmann, "Conducting polymer based amperometric enzyme electrodes", *Mikrochim. Acta*, 121 (1995), pp. 1–29.
T. Hoshi et al., "Controlled deposition of glucose oxidase on platinum electrode based on an avidin/biotin system for the regulation of output current of glucose sensors", *Anal Chem.* 67 (1995), pp. 770–774.

M. Trojanowicz and T. K. vel Krawezyk, "Electrochemical biosensors based on enzymes immobilized in electropolymerized films", *Mikrochim. Acta*, 121 (1995), pp. 167–181.
J. Wang, "Electroanalysis and biosensors", *Anal. Chem.* 67 (1995), pp. 487R–492R.
P. N. Bartlett and J. M. Cooper, "A review of the immobilization of enzymes in electropolymerized films", *J. Electroanalytical Chem.* 362 (1993), pp. 1–12.
J. Anzai et al., "Enzyme multilayer modified biosensors. Use of streptavidin and diglycosylated avidin for constructing glucose oxidase and lactate oxidase multilayers", *Anal. Sci.* 13 (1997), pp. 859–861.
J. Anzai et al., "Use of the avidin–biotin system for immobilization of an enzyme on the electrode surface", *Sensors and Actuators B*, 13–14 (1993), pp. 73–75.

(List continued on next page.)

Primary Examiner—Nathan M. Nutter
(74) Attorney, Agent, or Firm—Ladas and Parry

(57) ABSTRACT

The invention pertains to an electrically conductive copolymer of the general formula I:

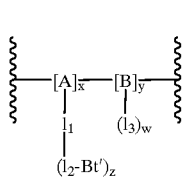

wherein
A is a first polymerizable monomer which produces an electrically conductive polymer when polymerized, and represents a polymerized unit of said monomer A in the electrically conductive polymer;
B is a second polymerizable monomer which when copolymerized with monomer A produces an electrically conductive polymer, and represents a polymerized unit of said monomer B in the electrically conductive polymer;
w is an integer greater than or equal to 0;
x is an integer greater than or equal to 1;
y is an integer greater than or equal to 0;
z is an integer greater than or equal to I;
$l_1$, and $l_2$ are each independently covalent linkers or spacer arms;
$l_3$ is substituent group having a desired chemical functionality; and
Bt' is selected from the group consisting of biotin and complexes of biotin with a molecule selected from the group consisting of avidin, streptavidin, derivatives of avidin and derivatives of streptavidin,
wherein said avidin, streptavidin, derivatives of avidin or derivatives of streptavidin may optionally be substituted, and said biotin, whether in free form or in the form of a complex, is covalently bonded to $l_2$. A process for forming the copolymer of invention, electrodes coated with the copolymer, as well and biochips or biosensors incorporating the copolymer of the invention, are also provided.

38 Claims, 7 Drawing Sheets

OTHER PUBLICATIONS

Heiduschka et al., "Microstructured peptide–functionalised surfaces by electrochemical polymerisation", *Chem. Eur. J.*, vol. 2, No. 6 (1996), pp. 667–672.

S. Cosnier et al., "Oxidative electropolymerization of polypyridinyl complexes of ruthenium(II)–containing pyrrole groups", *J. Electroanal. Chem.* 193 (1985), pp. 193–204.

S. Cosnier, "Electropolymerization of amphiphilic monomers for designing amperometric biosensors", *Electroanalysis*, vol. 9 No. 12 (1997), pp. 894–902.

S. Cosnier and A. Lepellec, "Poly(pyrrole–biotin): a new polymer for biomolecule grafting on electrode surfaces", *Electrochimica Acta*, 44 (1999), pp. 1830–1836.

S. Cosnier et al. "Electrogeneration of biotinylated functionalized polypyrroles for the simple immobilization of enzymes", *Electroanalysis*, vol. 10 No. 12 (1998) pp. 808–13.

Y. Kajiya et al., "Glucose sensitivity of polypyrrole films containing immobilized glucose oxidase and hydroquinone-sulfonate ions", *Anal. Chem.*, 63 (1991) pp. 49–54.

G. Jobst et al., "Thin–film microbiosensors for glucose–lactate monitoring", *Anal. Chem.*, 68 (1996) pp. 3173–3179.

L. M. Torres–Rodriquez et al., "Synthesis of a biotin functionalized pyrrole and its electropolymerization: toward a versatile avidin biosensor", *Chem. Commun.*, (1998), pp. 1993–1994.

ELECTRICALLY CONDUCTIVE COPOLYMERS AND THEIR PREPARATION

FIELD OF THE INVENTION

This invention concerns copolymers useful in the preparation of biochips and biosensors, as well as the preparation of such copolymers.

BACKGROUND OF THE INVENTION

For three decades, biosensors have been the subject of increasing research efforts and constitute now a major component of mainstream analytical chemistry (see e.g. Turner et al. (Eds.), Biosensors: Fundamentals and Applications, Oxford University Press, New York, 1987; Guilbault et al. (Eds.), Uses of Immobilized Biological Compounds, vol. 252, NATO ASI, Kluver Academic Publishers, 1993; Wang, Anal. Chem. 67 (1995) 487 R.) Considerable effort has been devoted in particular to develop optimized techniques for immobilizing biomolecules on suitable supports. Since miniaturized transducers are gaining importance, much attention is focused on the development of procedures allowing the spatially controlled deposition of biomolecules (see e.g. Heiduschka et al., Chem. Eur. J. 2 (1996) 667; Jobst et al., Anal. Chem. 68 (1996) 3173.)

Among conventional immobilization procedures, only the entrapment of biomolecules in electrogenerated conducting polymer films offers a good spatial resolution (see e.g. Bartlett et al., J. Electroanal. Chem. 363 (1993) 1; Schuhmann, Mikrochim. Acta, 121 (1995) 1; Trojanowicz et al., Mikrochim. Acta, 121 (1995) 167; Cosnier, Electroanalysis, 9 (1997) 894). However, the biomolecule entrapment within electropolymerized films suffers from severe drawbacks. This method requires high concentrations of biomolecules in the aqueous electrolyte during the electropolymerization process. This is because biomolecule incorporation in the growing polymer is only due to the presence of enzyme in the immediate vicinity of the electrode surface. In addition, the physical entrapment in polymer films such as polypyrrole, polythiophene, polyacetylene or polyaniline, drastically reduces the accessibility to the immobilized biomolecule. The steric constraints generated by the surrounding polymer in particular may hinder the formation of specific antigen-antibody binding. Consequently, the electrochemical entrapment of biomolecules is not an ideal method for the fabrication of immunosensors.

Other relevant prior art is U.S. Pat. No. 5,837,859 to Teoule et al., incorporated herein by reference, and the corresponding WO 94/22889.

SUMMARY OF THE INVENTION

It is thus desired to provide an electrically conductive copolymer suitable for presenting a wide variety of biologically interesting molecules on a surface, especially in a surface array or matrix suitable for use in biosensor or biochip applications.

There is thus provided, in accordance with a preferred embodiment of the invention, an electrically conductive copolymer of the general formula I:

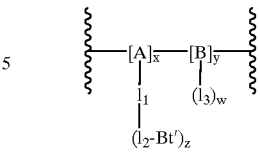

wherein
A is a first polymerizable monomer which produces an electrically conductive polymer when polymerized, and represents a polymerized unit of said monomer A in the electrically conductive polymer;

B is a second polymerizable monomer which when copolymerized with monomer A produces an electrically conductive polymer, and represents a polymerized unit of said monomer B in the electrically conductive polymer;

w is an integer greater than or equal to 0;
x is an integer greater than or equal to 1;
y is an integer greater than or equal to 0;
z is an integer greater than or equal to 1;
$l_1$ and $l_2$ are each independently covalent linkers or spacer arms;
$l_3$ is substituent group having a desired chemical functionality; and
Bt' is selected from the group consisting of biotin and complexes of biotin with a molecule selected from the group consisting of avidin, streptavidin, derivatives of avidin and derivatives of streptavidin, wherein said avidin, streptavidin, derivatives of avidin or derivatives of streptavidin may optionally be substituted, and said biotin, whether in free form or in the form of a complex, is covalently bonded to $l_2$.

By the term "covalent linker or spacer arm" is meant an atom or a chain of atoms covalently bonded to one another, covalently bonded at one end to the monomer and covalently bonded at the other end to the Bt group. The covalent linker or spacer arm may be branched and may contain functional groups, such as amine, amide, or carbonyl moieties. The covalent linker or spacer arm may thus be chosen to have a desired chemical functionality.

A "desired chemical functionality" may be any chemical property desired, such as but not limited to the ability to: prevent non-specific protein binding (e.g. polyethylene glycol chains, lipophilic chains or fluorinated chains); aid in electron transfer (e.g. viologen, quinone, polyaromatics, triaryl amine); affect magnetic properties (e.g. spin labels or paramagnetic complexes of rhuthenium); affect spin resonance; affect fluorescence quenching (e.g. dinitrophenyl or other aromatics); or imparting characteristics of hydrophobicity, hydrophilicity or amphipathicity.

Derivatives of avidin and streptavidin are avidin or streptavidin molecules subustituted by, bonded to or conjugated with other moieties or molecules, especially biomolecules. Thus avidin/streptavidin derivatives include, but are not limited to, avidin/streptavidin bonded or conjugated to: proteins (e.g. enzmies, antibodies, or receptors), peptides, sugars, oligosaccharides, nucleic acids, deoxynucleic acids, metal complexes, lipids, nitro ($-NO_2$) groups, and fluorophores.

The monomer A may be any polymerizable monomer which when polymerized yields an electrically conductive polymer. The monomer B may any polymerizable monomer which, when copolymerized with the monomer A, yields an electrically conductive polymer. Monomer B may thus be identical to monomer A. In accordance with a preferred embodiment of the invention, A and B are each independently selected from the group consisting of pyrrole, acetylene, azine, p-phenylene, p-phenylene vinylene, pyrene, thiophene, furan, selenophene, pyridazine, carbazole, aniline, and tyramide.

In accordance with an especially preferred embodiment of the invention, A and B are both pyrrole or both carbazole.

In accordance with a preferred embodiment of the invention, the ratio of x to y is in the range of about 1:0 to about 1:1,000,000.

In accordance with another preferred embodiment of the invention, $l_1$ and $l_2$ each independently contain functions selected from the group consisting of alkl groups, ether linkages, thioether linkages, carbonyl groups, carbon-carbon double bonds, carbon-carbon triple bonds, amide groups, sulfonamide groups, phosphate groups, thiophosphate groups, ketal groups and ester groups.

In accordance with a preferred embodiment of the invention, Bt is a complex of biotin with avidin or an avidin derivative, and said avidin or avidin derivative is substituted by at least one molecule selected from the group consisting of proteins, peptides, sugars, oligosaccharides, nucleic acids, deoxynucleic acids, metal complexes, lipids, nitro (—$NO_2$) groups, and fluorophores.

In accordance with a preferred embodiment of the invention, the copolymer is formed on a substrate comprising a modified electrode ME, said modified electrode comprising an electrode E and an electrically conductive monolayer M deposited on E, wherein M is a monolayer consisting of monomers B' each covalently bonded via a linker group $l_4$ to a functional group selected from the group consisting of thiol, symmetric disulfide, unsymmetric disulfide, and —$SiX_3$ wherein X is selected from Cl, I, Br, F, and $OR_3$ wherein each R is independently selected from H, $C_1$–$C_6$ alkyl, and aryl, with the proviso that when the functional group to which B' is bonded is $SiX_3$ then electrode E is an indium tin oxide electrode, and when the functional group to which B' is bonded is thiol or disulfide then E is a metallic electrode;

B' is a monomer B as defined above; and $l_4$ is a linker of 2 to 20 carbons length, optionally including ether linkages, thioether linkages, carbonyl groups, carbon-carbon double bonds, carbon-carbon triple bonds, amide groups, sulfonamide groups, phosphate groups, thiophosphate groups, ketal groups, and ester groups.

There is further provided, in accordance with another preferred embodiment of the invention, a process for preparing an electrically conductive copolymer of the formula I:

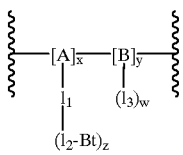

I wherein

A is a first polymerizable monomer which produces an electrically conductive polymer when polymerized, and as shown in formula I represents a polymerized unit of said monomer A in the electrically conductive polymer;

B is a second polymerizable monomer which when copolymerized with monomer A produces an electrically conductive polymer, and as shown in formula I represents a polymerized unit of said monomer B in the electrically conductive polymer;

w is an integer greater than or equal to 0;
x is an integer greater than or equal to 1;
y is an integer greater than or equal to 0;
z is an integer greater than or equal to 1;

$l_1$ and $l_2$ are each independently covalent linkers or spacer arms;

$l_3$ is substituent group having a desired chemical functionality; and

Bt is biotin covalently bonded to $l_2$, comprising the step of copolymerizing a monomer of the formula II $$A-l_1-(l_2\text{-}Bt)_z \qquad \text{II}$$

wherein A is a first polymerizable monomer which produces an electrically conductive polymer when polymerized, and $l_1$, $l_2$ and z are as hereinabove defined, with a monomer of the formula III $$B-(l_3)_w \qquad \text{III}$$

wherein B is a second polymerizable monomer which when copolymerized with monomer A produces an electrically conductive polymer, and $l_3$ and w are as hereinabove defined, on a support, wherein said copolymerizing is effected by electrochemical polymerization or by chemical polymerization.

In one preferred embodiment of the invention, the monomer of formula II is prepared by chemical or enzymatic synthesis. In another preferred embodiment of the invention, the monomer of formula m is prepared by chemical or enzymatic synthesis.

In a preferred embodiment of the invention, the copolymerization is effected by chemical polymerization using an oxidizing agent. When chemical polymerization using an oxiding agent is employed, any suitable oxidizing agent may be used. In a preferred embodiment of the invention, the oxidizing agent is selected from the group consisting of $FeCl_3$, $PbO_2$, $KMnO_4$, $MnO_2$, $CrO_3$, and pyridine complexes.

In a preferred embodiment of the invention the support is an electrically conductive support. In one preferred embodiment of the invention, the electrically conductive support is selected from the group of a metal, glass coated by a metal layer and plastic coated by a metal layer. The metal may be any suitable metal. In a preferred embodiment of the invention, the metal is selected from the group consisting of gold, copper, iron, platinum, palladium, indium, nickel, indium tin oxide, chromium, and silver.

In a preferred embodiment of the invention, the process further comprises the step of forming a complex between said biotin and a compound selected from the group of avidin, streptavidin, a derivative of avidin and a derivative of streptavidin, after said copolymerizing step, wherein said avidin, streptavidin, derviative of avidin or derivative of streptavidin may optionally be substituted, whereby to form a first film of avidin, streptavidin, avidin derivative or streptavidin derivative.

In another preferred embodiment of the invention, the process comprises the additional steps of (a) contacting the first film with biotin whereby to form a second film;

(b) optionally, contacting the second film with a compound selected from avidin, streptavidin, a derivative of avidin and a derivative of streptavidin, whereby to form a third film; and (c) optionally repeating steps (a) and (b) as desired to form a multilayered film on said copolymer of formula L wherein the outermost layer of said multilayered film may be a layer of avidin, avidin derivative, streptavidin, streptavidin derivative, or biotin.

In accordance with a preferred embodiment of the invention, the process comprises contacting the first film with biotin substituted with a ligand. In another preferred embodiment of the invention, the said outermost layer is a layer of avidin, an avidin derivative, streptavidin or a streptavidin derivative, and the process further comprises contacting the outermost layer with biotin or biotin substituted with a ligand. In a preferred embodiment of the invention, said ligand is selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

In accordance with a preferred embodiment of the invention, different areas of the first film or the outermost layer (when the outermost layer is a layer of avidin, streptavidin, or a derivative of avidin or streptavidin) of the multilayered film are contacted with biotin substituted with different ligands which can function as probes, whereby to form a matrix of probes. In another preferred embodiment of the invention, the outermost layer is a layer of biotin, and the process comprises further comprising contacting said outermost layer with a compound selected from avidin substituted with a ligand, a derivative of avidin substituted with a ligand, streptavidin substituted with a ligand and a derviative of streptavidin substituted with a ligand. In a preferred embodiment of the invention, the ligands are selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

In accordance with a preferred embodiment of process of the invention, A and B are each independently selected from the group consisting of pyrrole, acetylene, azine, p-phenylene, p-phenylene vinylene, pyrene, thiophene, furan, selenophene, pyridazine, carbazole, aniline, tyramide. In an especially preferred embodiment of process A and B are both pyrrole or both carbazole.

In a preferred embodiment of process of the invention, the ratio of x to y is in the range of 1:0 to 1: 1,000,000.

In a preferred embodiment of process of the invention, $l_1$ and $l_2$ each independently contain functions selected from the group consisting of alkyl groups, ether linkages, thioether linkages, carbonyl groups, carbon-carbon double bonds, carbon-carbon triple bonds, amide groups, sulfonamide groups, phosphate groups, thiophosphate groups, ketal groups, and ester groups.

In a preferred embodiment of process of the invention, said support comprises a modified electrode NE comprising an electrode E and an electrically conductive monolayer M deposited on E, wherein M is a monolayer consisting of monomers B' each covalently bonded via a linker group $l_4$ to a functional group selected from the group consisting of thiol, symmetric disulfide, unsymmetric disulfide, and $SiX_3$ wherein X is selected from Cl, I, Br, F, and $OR_3$ wherein each R is independently selected from H, $C_1$–$C_6$ alkyl, and aryl, with the proviso that when the functional group to which B' is bonded is SiX3 then electrode E is an indium tin oxide electrode, and when the functional group to which B' is bonded is thiol or disulfide then E is a metallic electrode;

B' is a monomer B as defined in claim 10;

and $l_4$ is a linker of 2 to 20 carbons length, optionally including ether linkages, thioether linkages, carbonyl groups, carbon-carbon double bonds, carbon-carbon triple bonds, amide groups, sulfonamide groups, phosphate groups, thiophosphate groups, ketal groups, and ester groups.

In accordance with a preferred embodiment of the invention, the monomer of formula II (in the process of the invention) or the group A-$l_1$-$l_2$-Bt' (in the copolymer of the invention) is selected from the group consisting of:

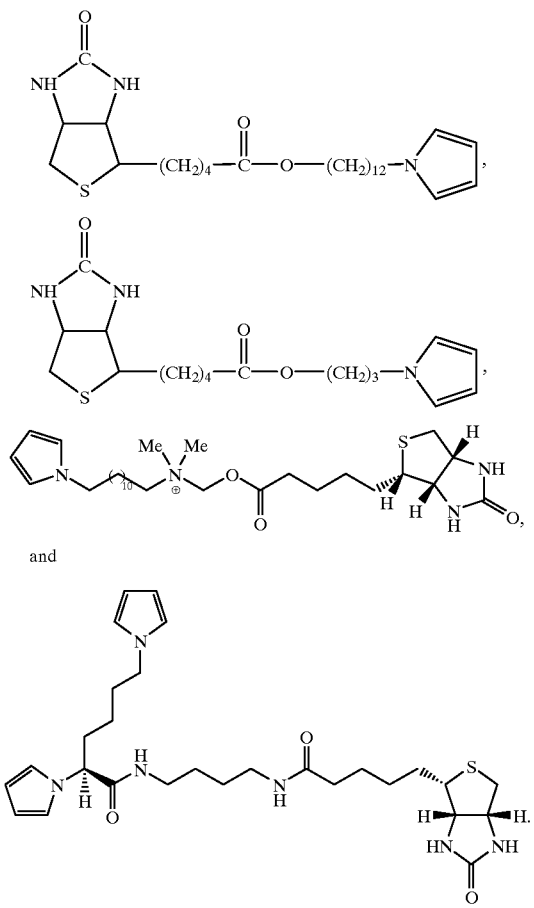

and

There is also provided in accordance with a preferred embodiment of the invention a biosensor or biochip comprising a copolymer of the invention.

There is also provided in accordance with a preferred embodiment of the invention an electrode coated with a copolymer of the invention.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
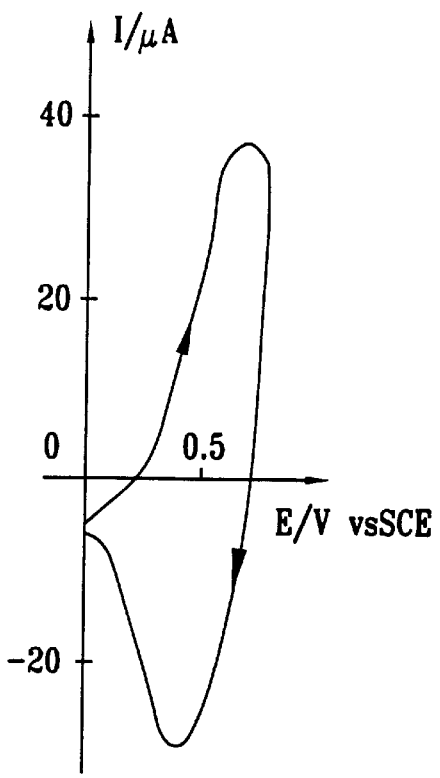
FIG. 1 is a cyclic voltammogram of an electrode coated with an electrically conductive copolymer in accordance with a preferred embodiment of the invention.

The invention will be better understood through the following illustrative and non-limitative description of preferred embodiments of the invention.

In the following examples, the following abbreviations are used:
AP: alkaline phosphatase
Av-AP: avidin-conjugated alkaline phosphatase
B-GOD: biotin-labeled glucose oxidase
DCC: dicyclohexylcarbodiimide
DMAP: dimethylaminopyridine
GOD: glucose oxidase
HP: horseradish peroxidase
QCM: quartz crystal microbalance
TBAP: tetrabutylammonium perchlorate
PPO-B biotine-labeled polyphenol oxidase
PPO: polyphenol oxidase

EXAMPLE 1
Step 1: Preparation of the bipyrrole derivative 1

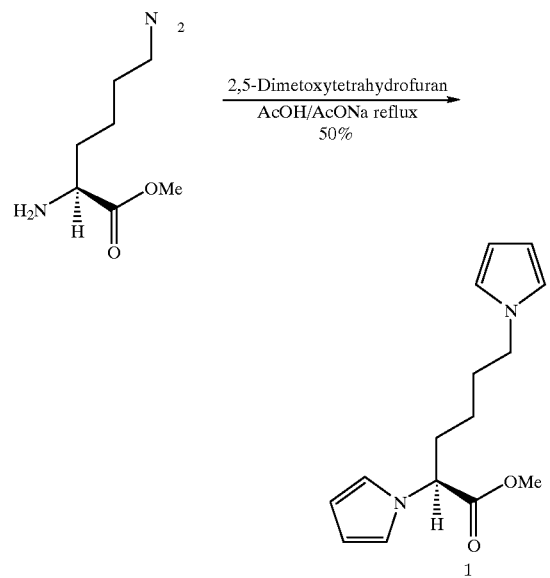

L-Lysine methyl ester dihydrochloride (700 mg, 3 mmol) and sodium acetate (500 mg, 6 mmol) were partially dissolved in acetic acid (10 ml) under a nitrogen atmosphere. 2,5-Dimethoxytetrahydrofuran (880 ml, 6.8 mmol) was added and the reaction mixture was heated to reflux with stirring for 3 hours. The reaction mixture was filtered and evaporated. The residue was dissolved in dichloromethane (250 ml) and the organic layer was washed with $NaHCO_3$ 10% (100 ml) and then with water (3×100 ml). After drying over magnesium sulfate and evaporation of the solvent, a brown oil was obtained The crude product was purified by chromatography (Silica Gel 60, 20 g, 10×2.5 cm, petroleum ether/ethyl acetate 8/1). A pale yellow oil was obtained (m=395 mg, yield=50%).

$^1$H-NMR ($CDCl_3$, 200 MHz): δ (ppm)=6.71 (t, J=2.1 Hz, 2H), 6.59 (t, J=2.1 Hz, 2H), 6.18 (t, J=2.1 Hz, 2H), 6.12 (t, J=2.1 Hz, 2H), 4.51 (dd, J=5.9 Hz, 9.6Hz, 1H), 3.82 (t, J=7.0 Hz, 2H), 3.7 (s, 3H), 2.11-1.19 (m, 6H).

$^{13}$C-NMR ($CDCl_3$): δ (ppm)=120.3 ($CH_{60}$), 119.9 ($CH_α$), 108.7 ($CH_β$), 107.9 ($CH_β$), 61.7 (CH), 49.1 ($CH_2$), 32.4 ($CH_2$), 30.9 ($CH_2$), 23.1 ($CH_2$).

MS (CI, $CH_4^+$): 261 (M+H)$^+$.

IR(v, cm$^{-1}$): 1736 (s, C=O); 1502 (m), 1482 (m), 1433 (m), 1279 (m), 1198 (m), 1087 (m).

Step 2: Preparation of the corresponding carboxylic acid derivative 2.

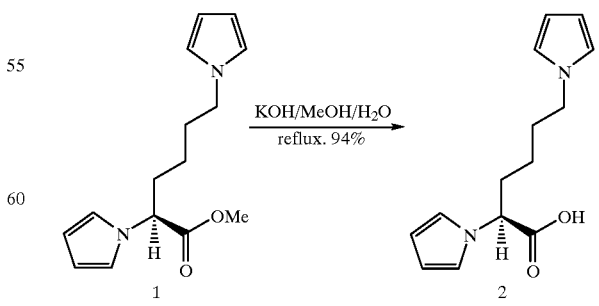

To the solution of 1 (1.5 g, 5.77 mmol) in methanol (55 ml) was added sodium hydroxyde aqueous solution (1.2 equivalent, 277 mg in 12 ml of water). The reaction mixture was refluxed 3 hours, cooled and poured into 150 ml of water. This aqueous solution was washed with ether (3×100 ml) and acidified with HCl 1N to pH 2. Extraction with ether (4×75 ml) and drying over magnesium sulfate gave a yellow oil which was purified by chromatography (Silica Gel 60, 50 g, 20×3.5 cm, dichloromethane/ethanol 9/1). A pale yellow oil was obtained (m=1.33 g, yield=94%).

$^1$H-NMR (CDCl$_3$, 200 ): δ (ppm)=9.24 (broad, 1H), 6.69 (t, J=2.15 Hz, 2H), 6.59 (t, J=2.10 Hz, 2H), 6.19(t,J= 2.15 Hz, 2H), 6.12 (t,J=2.10 Hz, 2H), 4.52 (dd, J=9.55 Hz, 5.87 Hz, 1H), 3.80 (t, J=7.04 Hz, 2H), 2.17-1.16 (m, 6H).

Step 3: Preparation of the activated ester 3.

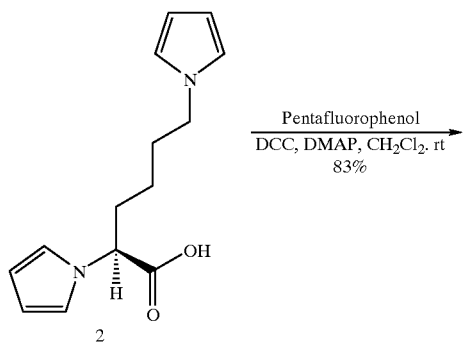

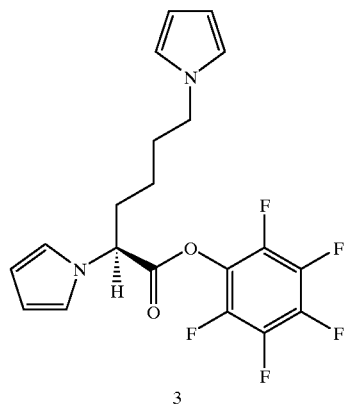

Under nitrogen, 2 (1.33 g, 5.43 mmol) was dissolved in dichloromethane (20 ml). Pentafluorophenol (996 mg, 5.43 mmol), dicyclohexyl-carbodiimide (1.312 g, 6.51 mmol), and catalytic 44methylaminopyridine (7 mg, 0.06 mmol) were added. The reaction mixture was stirred for 3 hours, filtrated and evaporated. The crude product was purified by chromatography (Silica Gel 60, 50 g, 20 x 3.5 cm, dichloromethane). A pale yellow oil was obtained (m=1.86 g, yield =83 %).

$^1$H-NMR (CDCl$_3$, 200 MHz): δ (ppm)=6.77 (t, J=2.1 Hz, 2H), 6.61 (t, J=2.1 Hz, 2H), 6.24 (t, J=2.1 Hz, 2H), 6.13 (t, J=2.1 Hz, 2H), 4.87 (dd, J=6.0 Hz, 9.3 Hz, 1H), 3.86 (t, J=6.9 Hz, 2H), 2.33-1.33 (m, 6H).

$^{13}$C-NMR (CDCl$_3$, 200 MHz): δ (ppm)=166,8 (C=O), 120.4 (CH), 120.00 (CH$_\alpha$), 109.55 (CH$_\beta$), 108.17 (CH$_\beta$), 61.07 (CH), 49.11 (CH$_2$), 32.27 (CH$_2$), 30.90 (CH$_2$), 23.07 (CH$_2$).

Step 4: Preparation of the bipyrroleamine derivative 4.

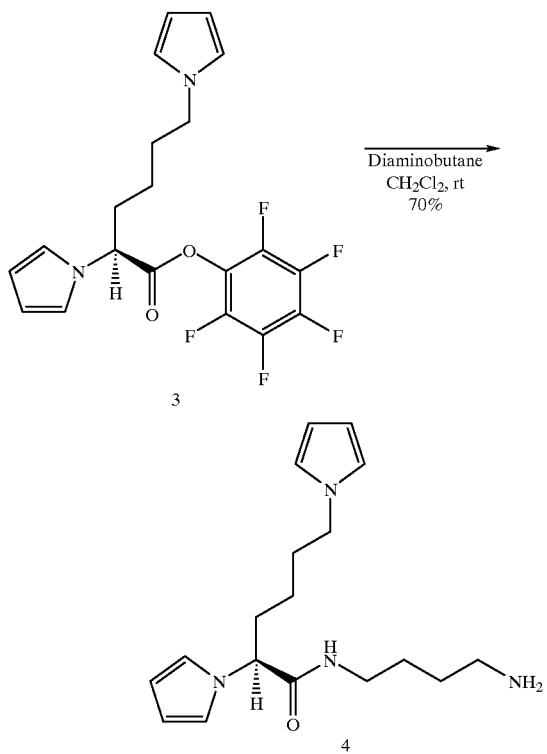

Under nitrogen, 3 (200 mg, 0.48 mmol) was dissolved under nitrogen in dichloromethane (10 ml). Diaminobutane (210 mg, 2.39 mmol) was added and the reaction mixture was stirred for 2 hours and poured into 40 ml of dichloromethane. The organic layer was washed with water (4×50 ml), dried over magnesium sulfate and evaporated. The crude product was purified by chromatography (Silica Gel 60, 25 g, 10×2.5 cm, ethanol/triethylamine 98/2). A colorless oil was obtained (m=106 mg, yield=70 %).

$^1$H-NMR (CDCl$_3$, 500 MHz): δ (ppm)=6.66 (t, J=2.1 Hz, 2H), 6.59 (t, J=2.1 Hz, 2H), 6.23 (t, J=2.1 Hz, 2H), 6.11 (t, J=2.1 Hz, 2H), 5.96 (broad, 1H), 4.40 (dd, J=11.0 Hz, 4.4 Hz, 1H), 3.82 (t, J=7.1 Hz, 2H), 3.16 (t, J=5.8, 2H), 2.64 (t, J=6.7 Hz, 2H), 1.96-1.13 (m, 10H).

Step 5: Preparation of the bipyrrole-biotin derivative 5.

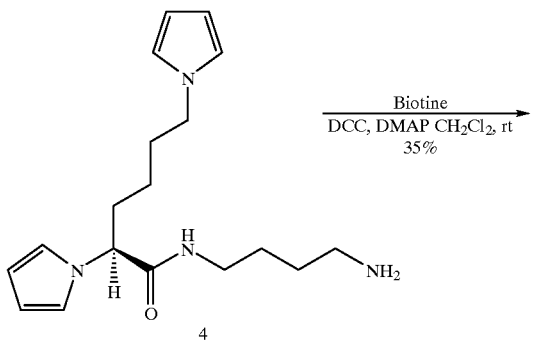

-continued

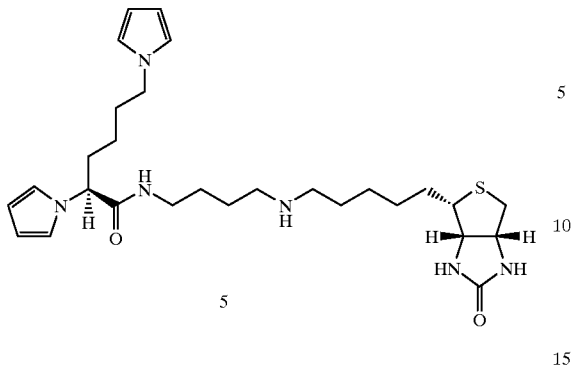
5

Under nitrogen, 4 (90 mg, 0.28 mmol) was dissolved in dichloromethane (4 ml). d-Biotin (69 mg, 0.28 mmol), dicyclohexyl-carbodiimide (72 mg, 0.36 mmol) and catalytic 4-dimethylaminopyridine (3 mg, 0.025 mmol) were added. The reaction mixture was stirred 5 days and filtered. The crude product was purified by chromatography (Silica Gel 60, 30 g, 10×2.5 cm, ethanol). A colorless oil was obtained (m=53 mg, yield=35 %).

$^1$H-NMR (DMSO, 200 MHz):δ (ppm)=8.12 (t, J=5.3 Hz, 1H), 7.77 (t, J=5.4 Hz, 1H), 6.76 (t, J=2.1 Hz, 2H), 6.67 (t, J=2.1 Hz, 2H), 6.43 (broad, 1H), 6.37 (broad, 1H), 5.95 (t, J=2.1 Hz, 2H), 5.93 (t, J=2.1 Hz, 2H), 4.49 (t, J=7.5 Hz, 1H), 4.28 (m, 1H), 4.10 (m, 1H), 3.79 (t, J=7.0 Hz, 2H), 3.43 (m, 1H), 3.00 (m, 4H), 2.80 (m, 1H), 2.56 (m, 1H), 2.03, (t, J=2.3 Hz, 2H) 1.96-1.22 (m, 16H).

EXAMPLE 2
Step 1: Preparation of the bromoalkylpyrrole derivative 6

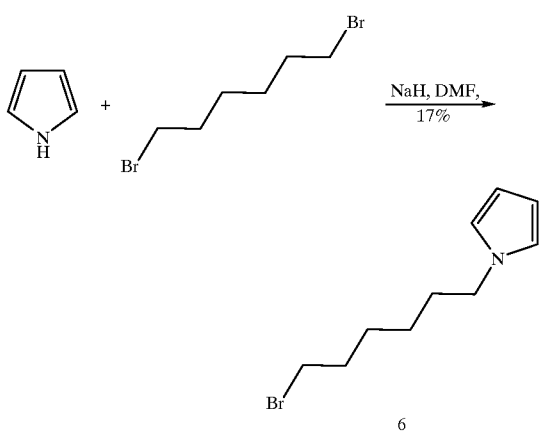

Under a nitrogen atmosphere, to a solution of pyrrole (1.6 ml, 24 mmol) in dimethylformamide (15 ml) was added sodium hydride (0.5 g, 21 mmol). The solution was stirred one hour and 7.5 ml of this solution was introduced under nitrogen atmosphere in the solution of dibromohexane (4 ml, 27.3 mmol) in dimethylformamide (10 ml). The reaction mixture was left to react overnight at room temperature and was poured in water (50 ml). The aqueous solution was extracted with ether (3×15 ml) and the organic layer was washed with water (2×50 ml), dried on magnesium sulfate and evaporated A yellow-brownish oil was obtained . The crude product was purified by chromatography (Silica Gel 60, 100 g, 23×3.5 cm, petroleum ether/ethyl acetate 99/1). A pale yellow oil was obtained (m=481 mg, yield=17 %).

$^1$H-NMR (CDCl$_3$, 200 MHz): δ (ppm)=6.64 (t, J=2.1 Hz, 2H), 6.14 (t, J=2.1 Hz, 2H), 3.88 (t, J=7.0 Hz, 2H), 3.39 (t, J=6.7 Hz, 2H), 1.25-1.88 (m, 8H).

Step 2: Preparation of the thiol derivative 7.

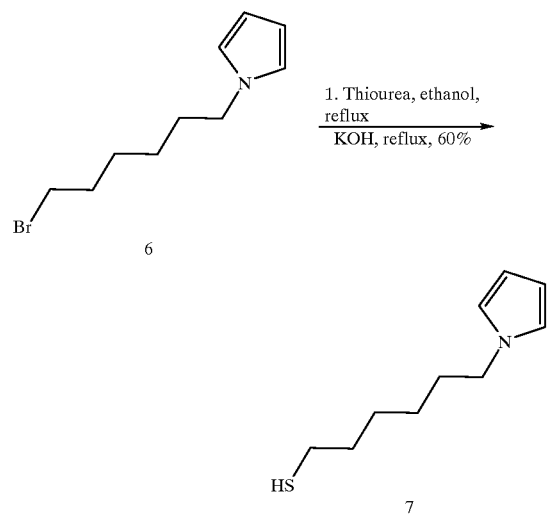

Under a nitrogen atmosphere, bromoalkylpyrrole (650 mg, 2.95 mmol) was added to the solution of thiourea (410 mg, 5.39 mmol) in ethanol (25 ml). The reaction mixture was heated to reflux during 24 hours and evaporated. The thiouronium salt was dissolved in water (50 ml) and washed with ether (3×30 ml). Hydrolysis was performed under reflux of a potassium hydroxyde 10% solution during 2 hours. At 0° C., HCl 3N was added until pH=1 and the thiol derivative was extraxted with ether (3×30 ml), washed with water (3×50 ml), dried on magnesium sulfate and evaporated. The crude product was purified by chromatography (Silica Gel 60, 40 g, 20×2.5 cm, hexane/ethyl acetate 95/5). A pale yellow oil was obtained (m=323 mg, yield=60%)

$^1$H-NMR (CDCl$_3$, 200 MHz) δ (ppm) 6.64 (t, J =2.1 Hz, 2H), 6.13 (t, J=2.1, 2H), 3.87 (t, J=7.1 Hz, 2H), 2.51 (q, J=7.3 Hz, 2H), 1.17-1.84 (m, 8H).

$^{13}$C-NMR (CDCl$_3$): δ (ppm)=120.4 (CH$_\alpha$), 106.2 (CH$_\beta$), 49.5 (CH$_2$), 33.8 (CH$_2$), 31.4 (CH$_2$), 27.9 (CH$_2$), 26.2 (CH$_2$), 24.5 (CH$_2$).

MS (CI, CH$_4$$^+$): 184 (M+H)$^+$, 150 (M—SH)$^+$.

EXAMPLE 3
Preparation of Copolymer
Step 1: Preparation of pyrrole-modified biotin 8

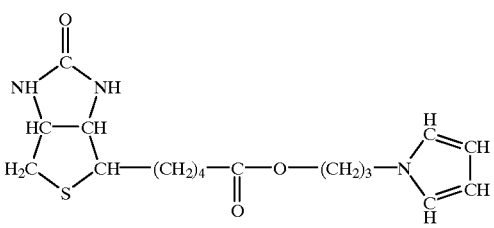

Avidin (chromatographically purified), glucose oxidase (GOD, 160 U mg$^{-1}$) and biotin-labeled glucose oxidase (B-GOD, 150 U mg$^{-1}$) were purchased from Sigma. The pyrrole monomer (3-pyrrol-1-yl-propyl) triethylammonium tetrafluoroborate (9) was synthesized as described in S. Cosnier et al., Electroanal. Chem. 271 (1989) 69.

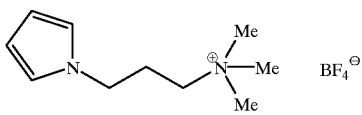

The biotin derivative 8 was synthesized in the following manner: biotin (500 mg, 2 mmol), 3-(1-pyrrolyl) propane 1-ol (208 mg, 1.66 mmol), DCC (413 mg, 2 mmol) and DMAP (81 mg, 0.66 mmol) were dissolved in dry $CH_2Cl_2$. The mixture was stirred under argon for 6 days at room temperature and then filtered. The organic phase was evaporated and the residue was washed with $Et_2O$. The resulting product was chromatographed on silica gel with $CH_2Cl_2$/EtOH (95:5). Crystallization from $CH_2Cl_2/Et_2O$ gave 70 mg of 8 (10% yield). The compound was characterized by $^1H$ NMR and mass spectroscopy.

Mass spectroscopy (e.i.): m/e (% rel. intensity) 351 (51), 227 (100).

$^1H$ NMR (DMSO-D6, 200 MHz) δ ppm: 1.14-1.5 (m, 6 H), 1.75 (m, 2 H), 2.04 (t, 2 H), 2.68 (m, 1H), 2.86 (m, 1H), 3.08 (m, 1H), 4 (m; 4H), 4.26 (m, 1H), 4.46 (m, 1H), 5.61 (s, 1H), 6.04 (s, 1H), 6.14 (m, 2H), 6.64 (m, 2H).

All other reagents used were of analytical reagent grade.

The electrochemical behaviour of the biotin derivative 8 (I mM) in argon-purged $CH_2Cl_2$+0.1 M TBAP, was investigated by cyclic voltammetry on a platinum electrode. The cyclic voltammogram of monomer 1 clearly shows an irreversible peak at 1.35 V due to the oxidation of the pyrrole group. However, repeatedly scanning the potential between 0 and 1.4 does not induce the appearance of the electrochemical response of the polypyrrole matrix while the current intensity of the oxidation peak decreases.

Step 2: Copolymerization

The electrochemical equipment used is described in Cosnier et al., J. Electroanal. Chem. 271 (1989) 69. Potentials are reported versus the aqueous saturated calomel electrode (SCE). The working electrodes were platinum disk (diameter 5 mm) polished with diamond paste.

The amperometric measurements were performed under stirred conditions in a thermostated cell at 25.0±0.2° C. The GOD activity was measured spectrophotometrically at 425 nm via an o-tolidine-peroxidase coupled system.

Poly (8–9) copolymer films were prepared by controlled potential (0.5 mC) oxidation at 1.25 V of I mM monomer 8 and 2 mM monomer 9 in $CH_2Cl_2$ containing 0.1 M TBAP. FIG. 1 shows the cyclic voltammogram exhibited by the resulting modified electrode upon transfer into a $CH_2Cl_1$±0.1 M TBAP solution free of monomers, at a scanning rate of 100 mV/s. The reversible oxidation wave around 0.55 V corresponds to the electrochemical response of the polypyrrole matrix. The apparent surface coverage of electropolymerized 8 and 9 monomers, $\Gamma_{1+2}=2.2\times10^{-9}$ mol/$cm^2$, was determined from the charge recorded under the polypyrrole wave.

Step 3: Formation of Avidin-Biotin Complex

Following electropolymerization to form poly(89), 40 μl avidin solution (1 mg/ml) was spread on the poly (8–9) electrode for 20 min. The resulting electrode was carefully washed with phosphate buffer and 40 μl of B-GOD (1 mg $ml^{-1}$) were spread on its surface for 20 min at 5° C. The resulting enzyme electrodes were thoroughly rinsed in distilled wated and incubated for 30 min in stirred phosphate buffer containing 10 mM glucose at 20° C. before use.

Figure 2:
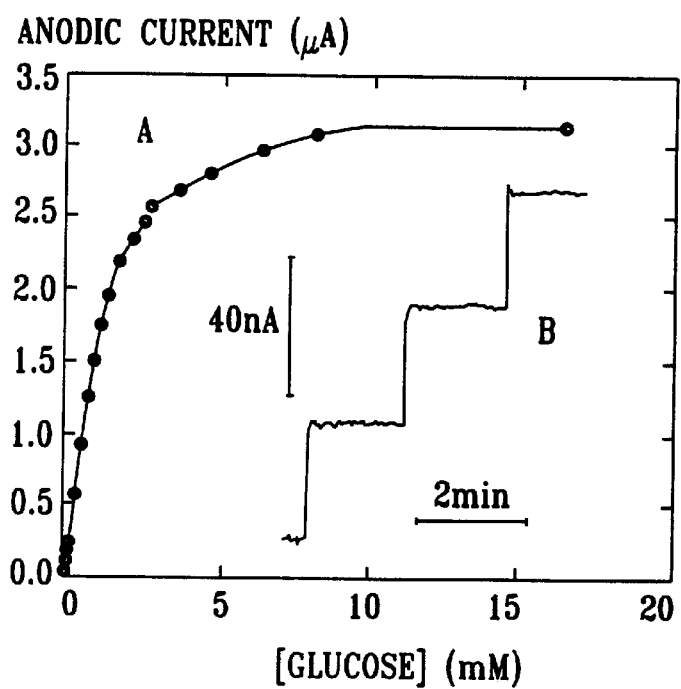
FIG. 2 shows the steady-state current-time responses of an electrode coated with an electrically conductive polymer complexed to an enzyme in accordance with a preferred embodiment of the invention as a function of glucose concentration.

After the successive deposition of avidin and B-GOD, the performance of the resulting enzyme electrode for the detection of glucose was investigated. For this purpose, the enzyme electrode was potentiostated at 0.6 V in 0.1 M phosphate buffer (pH 7) to detect the enzymically generated $H_2O_2$. Curve A in FIG. 2 presents the steady-state current response of the biosensor to successive increments (25 μM) of glucose concentration illustrating its fast response time (10 s). Curve B in FIG. 2 shows the amperometric current response of the enzyme electrode as a function of the glucose concentration. The calibration curve was linear up to 700 μM while a pseudoplateau was reached for higher concentrations (above 8 mM). The sensitivity of the biosensor (determined as the slope of the initial linear part of the calibration curve) is 7.0±0.1 mA $M^{-1}$ $cm^{-2}$.

In order to determine the nature of the enzyme attachment on the poly (1–2) electrode, a control experiment was carried out with a poly (1–2) electrode treated successively with avidin and native GOD. The replacement of B-GOD by native GOD induces a marked decrease in the glucose sensitivity (0.18 mA $M^{-1}$ $cm^{-2}$) of the biosensor. This suggests that the enzyme immobilization is mainly due to the avidin-biotin interactions instead of simple non specific adsorption. This glucose sensitivity is higher than that exhibited by biosensors based on a monolayer of B-GOD immobilized through the avidin-biotin system (1.5–4 mA $M^{-1}$ $cm^{-2}$, reported in Anzai et al., Denki Kagaku 64 (1993) 1141; Hoshi et al., Anal. Chem. 67 1995) 770; and Anazi et al., Anal. Sciences 13 (1997) 859).

The enzymatic activity of the poly (8–9)-avidin-B-GOD electrode (185 mU $cm^{-2}$) is markedly higher than those (1.5 and 125 mU $cm^{-2}$) reported for polypyrrole-GOD electrodes, e.g. in Foulds et al., J. Chem. Soc. Faraday Trans. 1 82 (1986) 1259 or Kajiya et al., Anal. Chem. 63 (1991) 49.

EXAMPLE 4

Preparation of Polymer and Multilayer Films

Step 1: Preparation of pyrrole-modified biotin 10

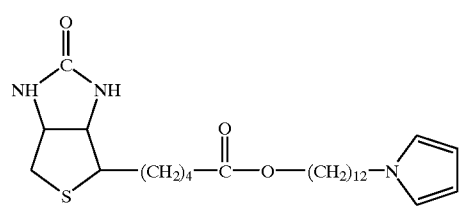

Biotin (500 mg, 2 mmol), 12-(1-pyrrolyl)dodecanol (417 mg, 1.66 mmol), DCC (413 mg, 2 mmol) and DMAP (81 mg, 0.66 mmol) were dissolved in dry deoxygenated $CH_2Cl_2$ (10 mL). The mixture was stirred at room temperature for 5 days under argon. The resulting solution was filtered and evaporated. After extraction 10 precipitated as a white solid. This crude product was then chromatographed on silica gel with a 95-5 $CH_2Cl_2$-$Et_2O$ mixture as eluting solvent, yielding 618 mg of 10 (78% yield). FAB-MS: 478 ([M+H]$^+$), 476 ([M-H]$^+$). $^1H$ NMR (200 MHz) (DMSO): δ 1.30–1.70 (m, 26 H), 2.25 (t, 2H), 2.58 (m, 1H), 2.88 (m, 1H), 3.08 (m, 1H), 3.82 (t, 2H), 4.00 (t, 2H), 4.12 (m, 1H), 4.30 (m, 1H), 5.95 (m, 2H), 6.35 (s, 1H), 6.40 (s, 1H), 6.70 (m, 2H).

Step 2: Polymerization

The electropolymerization of 10 and the electrochemical characterization of 10 and poly-10 film were run at room temperature under an argon atmosphere in a conventional three-electrode cell. Acetonitrile (Rathburn, HPLC grade) was used as received. Tetrabutylammonium perchlorate (TBAP) was recrystallized from ethyl acetate/cyclohexane and vacuum-dried at 80° C. three days before use. A 10 mM Ag/Ag$^+$ in $CH_3CN$ electrode was used as reference electrode in acetonitrile electrolyte and a saturated calomel electrode (SCE) was used as reference electrode in 0.1 M phosphate buffer. The working electrodes were platinum or glassy carbon disks (diameter 5 mm) polished with 1 $\mu$m diamond paste.

The electrochemical measurements were performed under stirred conditions in an air-saturated 0.1 M phosphate buffer solution (pH 6.5 or 7). These experiments were carried out in a conventional three-electrode cell thermostated at 30.0±0.1° C.

Figure 3:
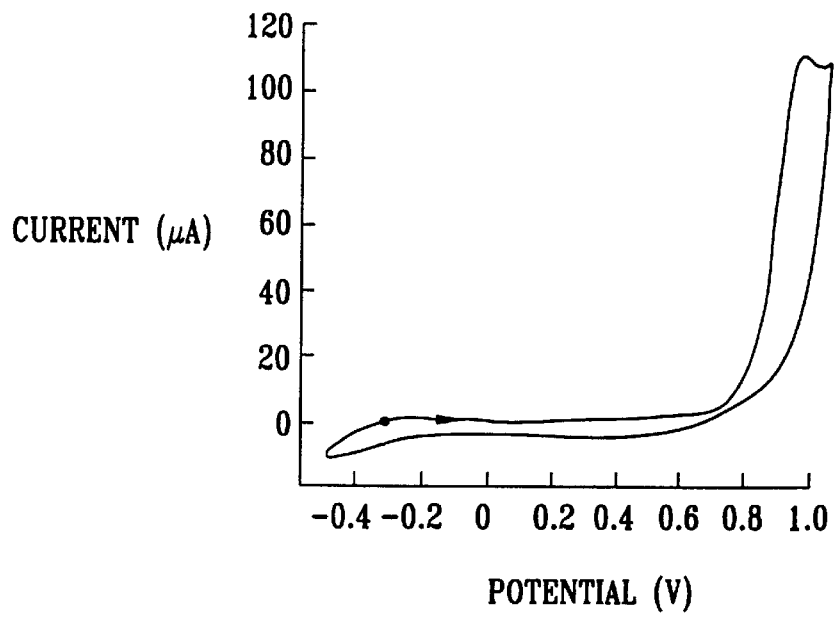
FIG. 3 shows the cyclic voltammogram of a monomer which can be used in accordance with a preferred embodiment of the invention.

Upon oxidative scanning, the cyclic voltammogram of 10 recorded in $CH_3CN$+0.1M TBAP displays an irreversible peak at 0.96 V due to the oxidation of the pyrrole group (FIG. 3). Electropolymerization of 10 was therefore accomplished by controlled potential oxidation at 0.8 V to prevent the overoxidation of the polypyrrole skeleton and hence to preserve its conductivity, using 2 mM monomer 10 in $CH_3CN$+0.1M TBAP.

Figure 4:
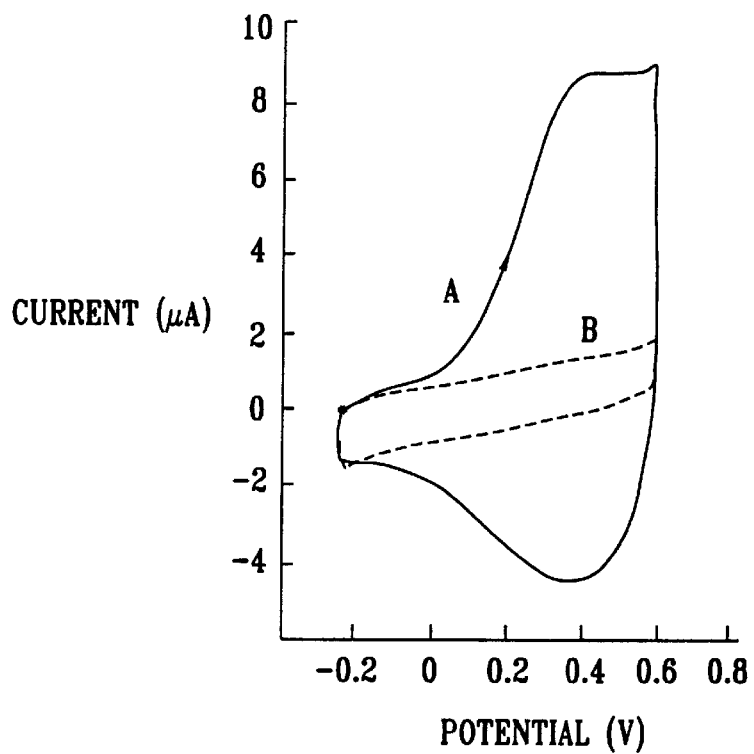
FIG. 4 is a cyclic voltammogram of an electrode coated with an electrically conductive polymer in accordance with a preferred embodiment of the invention.

The resulting electrode was transferred with thorough rinsing to a $CH_3CN$+0.1M TBAP solution free of monomer. As shown in FIG. 4, the cyclic voltammogram of this electrode exhibited a reversible oxidation wave around 0.4 V. This indicates the formation of an electropolymerized conducting film (poly-10) on the electrode surface. This behavior is quite typical of polypyrroles which become electronically conducting in the oxidized state. The apparent surface coverage of electropolymerized 10, $\Gamma_1$=7.3×10$^{-9}$ mol cm$^{-2}$, was determined from the charge recorded under the oxidation wave of the polypyrrole backbone. Owing to its conductivity, the amount of poly-10 film increases almost linearly with the charge passed during the electropolymerization step, and thus the thickness of the poly 10 films was controlled by integration of the electrical charge passed during the electropolymerization.

The modified electrodes were transferred in $CH_3CN$+0.1 M $LiCO_4$ in order to replace the initially incorporated cation (TBA$^+$) by the electrolyte cation (Li$^+$) by repeatedly scanning the electrode potential at 0.1 Vs$^{-1}$ over the polypyrrole oxidation wave. The polypyrrole electroactivity of the modified electrodes was destroyed by overoxidation at 1.3 V for 5 min.

Step 3: Binding of Avidin

Glucose oxidase-biotinamido-caproyl labeled (B-GOD) (from Aspergillus niger, 110 U mg$^{-1}$) was purchased from Sigma. Biotin-labeled polyphenol oxidase (PPO-B) was prepared as follows: 3 mg of PPO were dissolved in 0.6 mL of 0.1 M $NaHCO_3$. After complete dissolution of PPO, 45 $\mu$L of 0.25 M N-hydroxy-succinimidobiotin were added with constant stirring. The resulting solution was kept under constant stirring in the dark for an additional 60 min. The resulting biotinylated enzyme was purified in a Sephadex G25 column (1.0×12 cm) equilibrated and eluted with 5 mM Tris HCl, pH 7.0 and lyophilized.

The specific binding of avidin to the polymerized biotin sites was performed by depositing 20 $\mu$L of avidin solution (2 mg mL$^{-1}$) on the poly 1 disk electrodes (diameter 5 mm) for 30 min at 4° C. The resulting electrodes were carefully washed with phosphate buffer and 20 $\mu$L of B-GOD or PPO-B (1 mg mL$^{-1}$ in 1 mM phosphate buffer) were deposited on the electrode surfaces for 30 min at 4° C. The resulting enzyme electrodes were carefully rinsed in distilled water and incubated 30 min in stirred phosphate buffer (pH 6.5 or 7) to remove the nonspecifically bound PPO-B or B-GOD molecules.

The modification of the polymer surface by multiple layers of the avidin-biotinylated enzyme system was carried out by the successive deposition of avidin and biotinylated enzyme solutions following the preceding procedure.

Step 4: Analysis

Gravimetric measurements were carried out using a quartz crystal microbalance (QCM) in order to determine the affinity of the biotinylated polypyrrole film for avidin. In aqueous solutions, QCMs may be used to characterize quantitatively the binding event between a sensitive layer coated on the quartz surface and biological macromolecules. The QCM is an oscillating quartz crystal that displays a frequency response to a change in the mass as described by the following equation:

$$\Delta f = -f_o^2 \left( \frac{2}{S \times n \times (\sqrt{\mu\rho})} \right) \Delta m$$

where $\Delta f$ is the measured shift in frequency (Hz), S is the active area of the crystal (cm$^2$), $\rho$ is the quartz density (2.648 g.cm$^{-3}$), $\mu$ is the shear modulus (2.947 10$^{11}$g.s$^{-2}$ cm$^{-1}$), n the overtone number, $f_o$ is the fundamental crystal frequency and $\Delta m$ is the mass change on the surface of the crystal (g). Thus the employed 27 MFz QCM transducer exhibits a theoretical mass/frequency sensitivity of 360 pg.Hz$^{-1}$ (S=0.2 cm$^2$)

Figure 5:
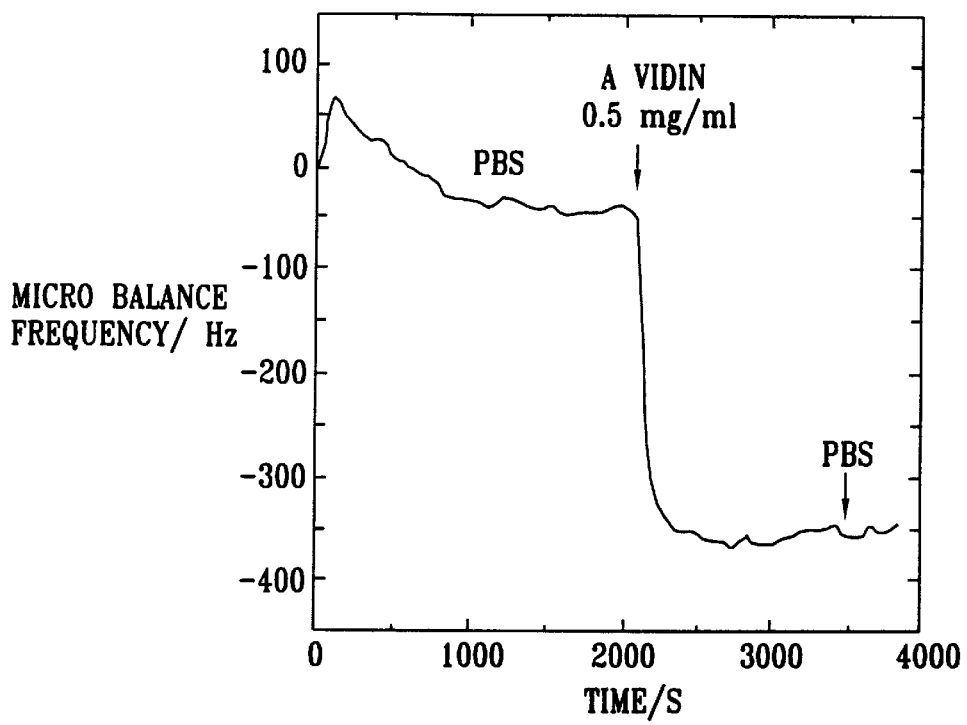
FIG. 5 shows the frequency response of a quartz crystal microbalance, constructed an operative in accordance with a preferred embodiment of the invention, to an increase in mass.

A poly-10 film ($\Gamma_1$ =1.33 10$^{-1}$ mol cm$^{-2}$) was electrogenerated onto one side (surface area 0.27 cm$^2$) of a gold-plated electrode of a QCM (an AT-cut 9 MHz quartz crystal (CQE, France) coated with two identical gold layers (2000 Å thick)). The poly-10 coated crystal electrode was then mounted between two O-ring seals inserted in a plexiglass cell, the poly-10 electrode being in contact with the solution. The flow-through cell (volume 50 $\mu$L) was associated with a micropump (P1, Pharmacia) allowing a constant flow rate of 60 $\mu$L min$^{-1}$. The 27 MHz QCM was coupled to a 9 MHz resonator (on the third overtone) and a frequency counter (HP 53132 A). This 27 MD QCM transducer exhibits a sensitivity of 360 pg Hz$^{-1}$. In the continuous-flow mode, the frequency shift was monitored for successive flow carriers: 0.01 M phosphate buffered saline (PBS) (pH 7.4, 137 nM NaC9 , 2.7 mM KCI), then PBS containing avidin (0.5 mg mL$^{-1}$), then PBS again. The frequency response of the QCM to the increase in mass as recorded in continuous-flow mode is shown in FIG. 5.

The same procedure was applied to a crystal modified by an electropolymerized poly(N-methylpyrrole) for checking the specificity of the biotinylated polymer. No changes in the frequency response of this modified QCM were observed in the presence of avidin.

The catalytic oxidation of glucose by GOD in the presence of dioxygen produces $H_2O_2$. Consequently the enzymatic activity of the immobilized B-GOD (i.e., the analytical capability for glucose determination of the biosensors of with various numbers of layers of avidin-B-GOD) was determined by measuring amperometrically the increase in $H_2O_2$ concentration. For this purpose, a Pt-electrode was immersed in stirred 0.1 M phosphate buffer (pH 7) containing glucose (50 mM) and potentiostated at 0.6 V. Then, the electrode modified by BGOD was soaked in the aqueous electrolyte and the increase in anodic current versus time was recorded The enzymatic activity of the biosensor was evaluated from the slope of the rectilinear part of the current vs. time dependence, by comparison with the slope obtained in the same conditions with the free enzyme.

Figure 6:
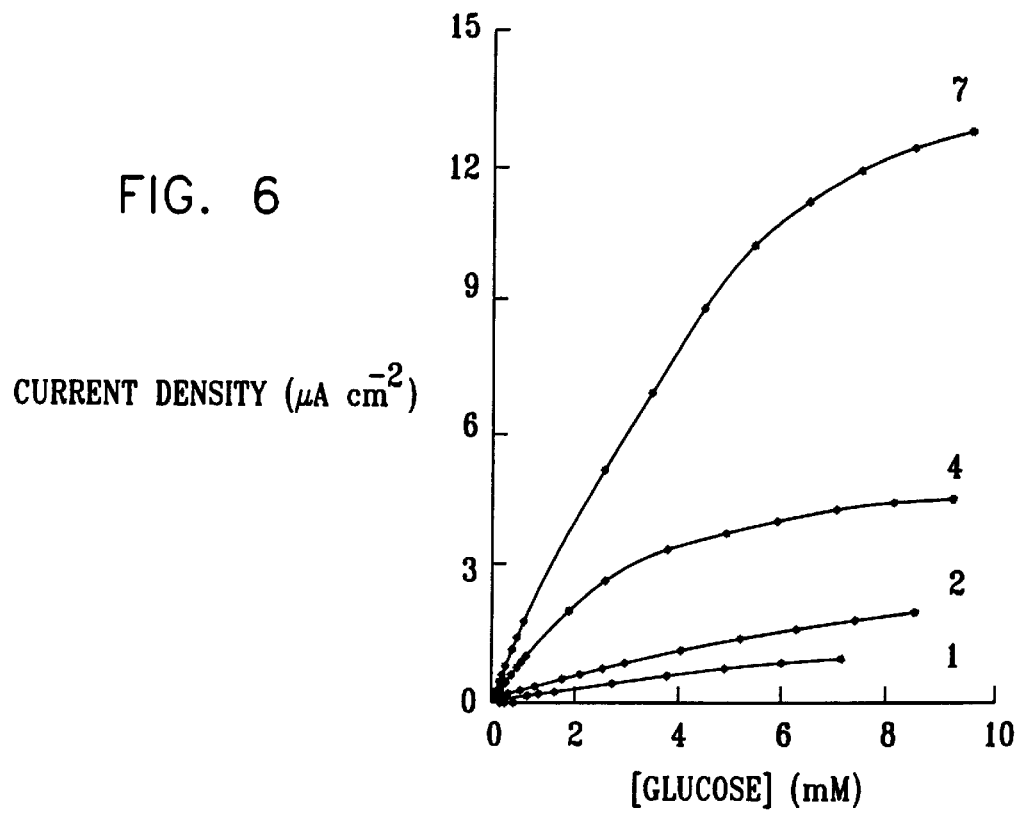
FIG. 6 shows shows the steady-state current-time responses of an electrode coated with an electrically conductive polymer complexed to an enzyme in accordance with a preferred embodiment of the invention as a function of glucose concentration.

FIG. 6 depicts the amperometric response of the biosensors as a function of glucose concentration. The calibration curves were quasi-linear with glucose concentration up to 2 mM and curved gradually at higher concentrations. As shown in Table 1, the biosensor sensitivity (determined as the slope of the initial linear part of the calibration curve) increases with the number of enzyme layers.

TABLE 1

Analytical characteristics of the poly-10 electrodes modified by different cycles of sequential deposition of avidin and B-GOD, for the determination of glucose.

| Number of monolayers | Biosensor sensitivity[a] (mA M$^{-1}$ cm$^{-2}$) | Enzymatic activity[b] (mU cm$^{-2}$) |
|---|---|---|
| 1 | 0.15 | 39 |
| 2 | 0.32 | 114 |
| 4 | 1.32 | 251 |
| 7 | 3.36 | 373 |

[a]Determined as the slope of the linear part of the calibration curves.
[b]Determined amperometrically from the time-dependent increase in $H_2O_2$ concentration at saturating glucose conditions.

In addition, the determination of $K^{app}_M$ of the biosensor for glucose from a Michaelis-Menten analysis of the glucose plot for each biosensor configuration showed the $K^{app}_M$ values remain almost constant (2–4 mM). This indicates the successive immobilization of enzyme layers exhibiting a similar kinetic behavior. It should be noted that the amperometric response of the biosensors are lower than their enzymatic activity.

Figure 7:
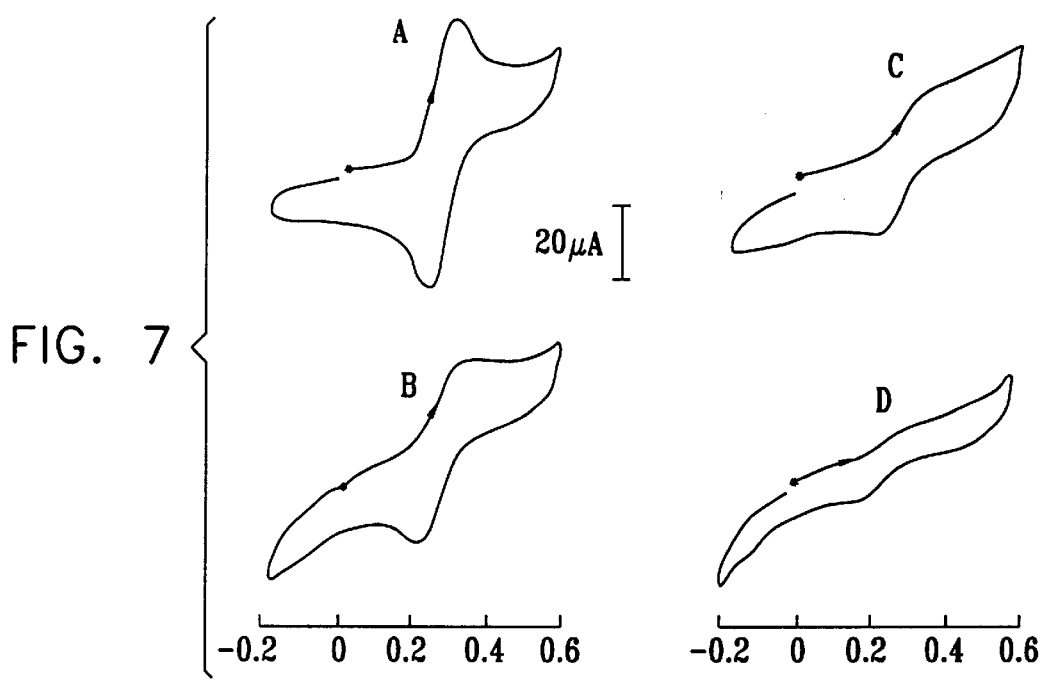
FIG. 7 shows cyclic voltammogras of various electrodes coated with copolymers or complexed copolymers in accordance with a preferred embodiment of the invention.

The evolution of the polymer permeability for the successive binding of avidin and biotinylated glucose oxidase (BGOD) was determined by recording the cyclic voltammogram of ferrocene carboxylic acid (Fc) used as a permeant electroactive probe. Since the electrochemical responses of the probe and polypyrrole backbone are close together, the polypyrrole electroactivity was destroyed by overoxidation to avoid mixing of the two signals (see FIG. 4). The cyclic voltammograms for Fc at a bare Pt electrode and at a poly-10 electrode ($\Gamma$=1.69×10$^{-9}$ mol cm$^{-2}$) are shown in curves A and B. respectively, of FIG. 7. The cyclic voltammograms for Fc at a poly-10 electrode after immersion in an avidin solution and subsequent immersion into a GOD-B solution are shown in curves C and D, respectively, of FIG. 7. FIG. 7, curves C and D, show a permeability diminution due to an increase in the thickness of the polymer layer. This illustrates successively the binding of avidin to the polymerized biotin moities and that of BGOD to avidin.

The storage stability of the poly-10 electrodes modified by 2-, 4- and 7-B&GOD layers, stored at 4° C. in 0.1 M phosphate buffer, was also examined, by periodically recording the current response of the biosensors with increasing concentration of glucose in the linear part of the calibration curve. The three biosensors exhibit the same behavior, namely an initial decrease in biosensor sensitivity to 50% of their initial values, followed by a stabilization in the range 20–25% for 15 days. These values remain almost constant after 38 and 64 days.

Figure 8:
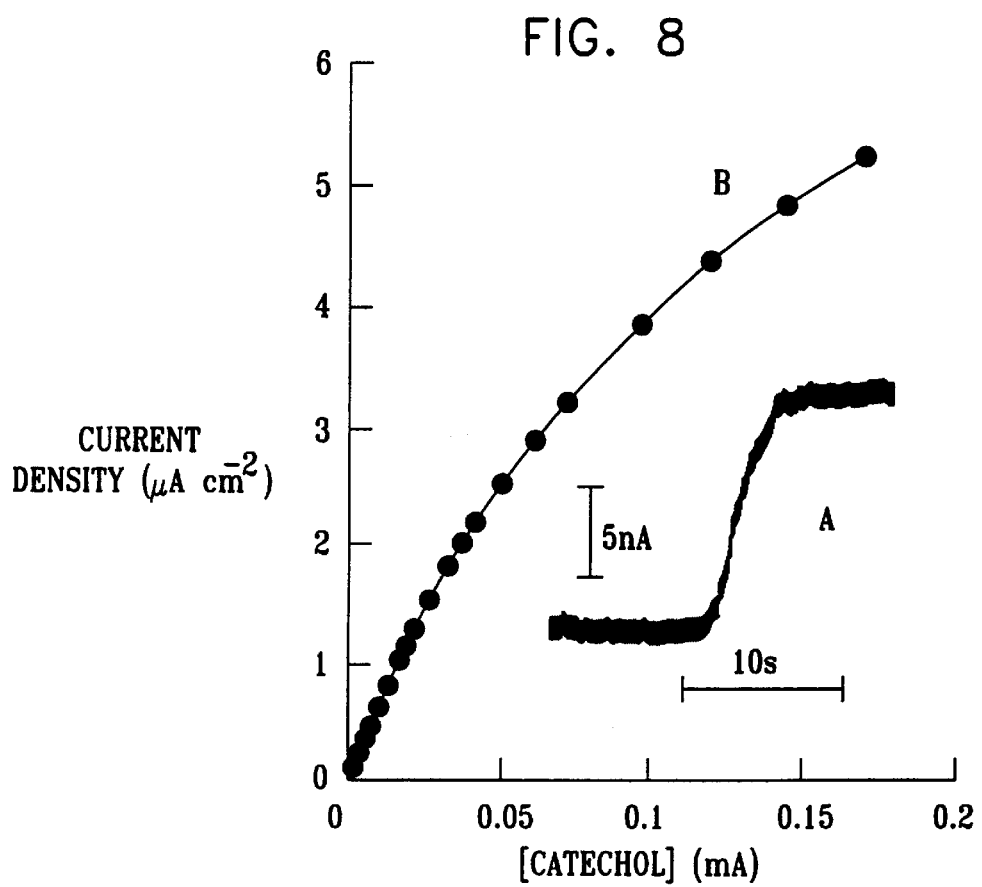
FIG. 8 shows the steady-state current response a biosensor constructed an operative in accordance with a preferred embodiment of the invention catechol concentration.

Polyphenol oxidase (PPO) catalyzes the oxidation of several monophenols and o-diphenols to o-quinones while reducing dioxygen to water. Following the preceding procedure of B-GOD immobilization, a biosensor configuration containing 5-enzyme layers of PPO-B was elaborated by successive deposition of avidin and PPO-B on a poly 10 electrode. The analytical characteristics of the biosensor have been determined in 0.1 M phosphate buffer (pH 6.5) by potentiostating the electrode at -0.2 V vs. SCE. Thus, the enzymatically produced o-quinones were reduced at the electrode surface generating an amperometric signal. The steady-state current response of this biosensor to an increment (1 $\mu$M) of catechol concentration is shown in FIG. 8, curve A. FIG. 8, curve B shows the amperometric current response of the biosensor as a function of catechol concentration The sensitivity of the biosensor and its detection limit (based on a signal-to-noise ratio of 3) are 65 mAM$^{-1}$ cm$^{-2}$ and 2×10$^{-7}$ M, respectively. This catechol sensitivity is markedly lower than that (1.5 AM$^{-1}$ cm$^{-2}$) obtained with biosensors based on PPO entrapped in a functionalized polypyrrole matrix[22]. The $K^{app}_M$ of the biosensor for catechol (0.15 mM), determined from a Michaelis-Marten analysis of the catechol plot, is similar to that reported by Barman, Enzyme Handbook, Vol. 1, p. 226, Springer-Verlag, N.Y. 1995 (0.24 mM) for the free enzyme, illustrating the non-denaturating character of the procedure of enzyme anchoring.

EXAMPLE 5

Step 1: Synthesis of pyrrole derivatives

The biotin-pyrrole derivative 8 was synthesized as described in Example 3. The polypyridyl ruthenium(II) complex 11 was synthesized as reported in Cosnier et al., J. Electroanal. Chem. 193 (1985) 193. The ruthenium complex exhibits a reversible metal-centered redox couple ($Ru^{II/III}$) at a potential (1.2 V) corresponding to the oxidation of pyrrole groups.

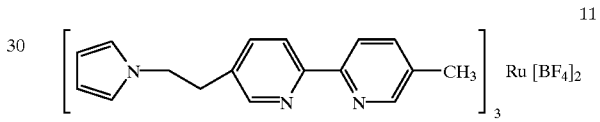

11

Step 2: Copolymerization

Figure 9:
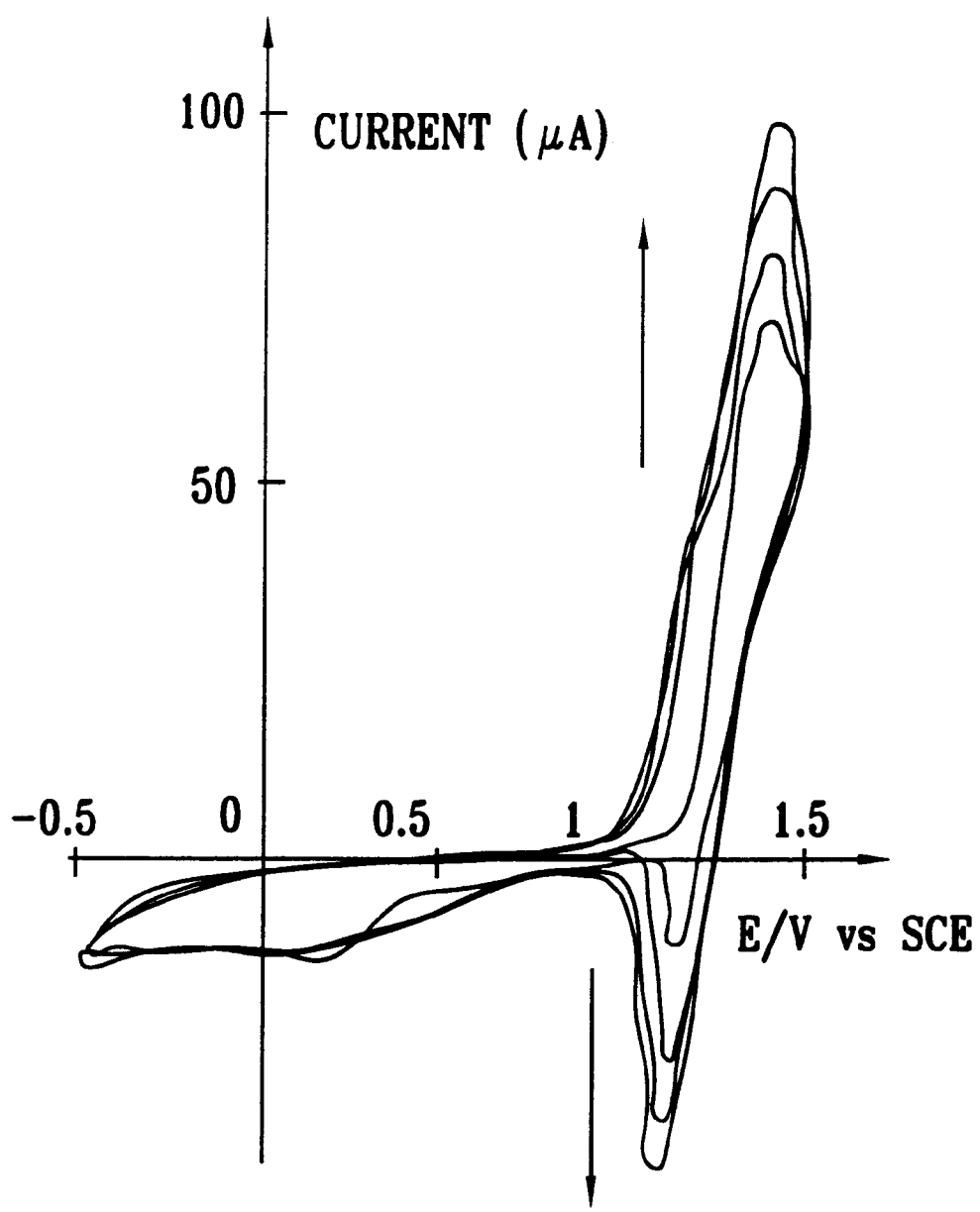
FIG. 9 shows a the oxidative potential of an electrode as it is coated with an electrically conductive polymer in accordance with a preferred embodiment of the invention, during repeated scans.

Poly(8–11) copolymer films were prepared by oxidative electropolymerization of a mixture of monomer 8 and monomer 11 by repeated potential scans between –0.5 and 1.5 V at a platinum electrode (diameter 5 mm) in $CH_2Cl_2$ containing 0.1 M TBAP. In order to modulate the copolymer composition, concentration ratios of 8/11 ranging from 0.5 to 6.7 were prepared, the total concentration of both monomers being constant (1 mM). The oxidative elctropolymerization of 0.5 mM of 8 and 0.5 mM of 11 by cycling the potential from –0.5 to 1.5 V is shown in FIG. 9.

Figure 10:
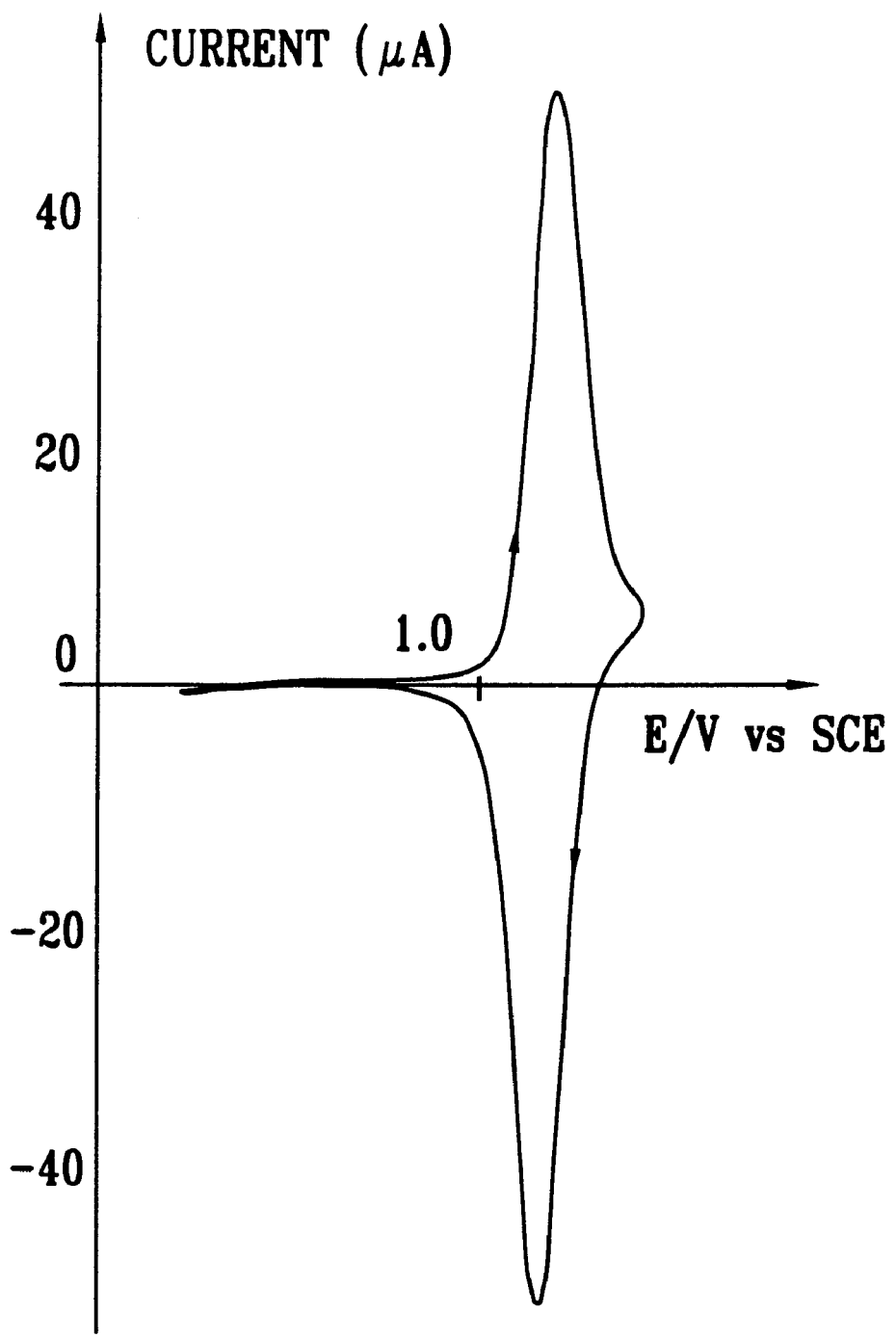
FIG. 10 shows a cyclic voltammogram of an electrode coated with an electrically conductive polymer in accordance with a preferred embodiment of the invention.

The redox conductivity of the copolymer enables sustained growth of the polymeric film. FIG. 10 depicts the cyclic voltammogram exhibited by the resulting modified electrode upon transfer into an electrolyte free of monomers. In the positive region, the poly (8–11) film presents the regular electroactivity of the ruthenium complex, thus this electrochemical signal can serve as a probe to evaluate the copolymer thickness. The apparent surface concentration of 11 ($\Gamma_2$) was calculated from the integrated charge under the Ru(II)/(III) oxidative or reductive peak. Taking account that the polymerization solution contains an equimolar mixture of 8 and 11, it can be assumed reasonably that the amount of electropolymerized 8 is of the same order of magnitude than the amount of poly 11. Since the bulkiness of 11 is markedly larger than that of 8, a monolayer of poly (8–11) film may be approximated to a monolayer of poly 11 film which corresponds to 8×10$^{-11}$ mol cm$^2$ [27].

For instance, the apparent surface coverage of the polymerized ruthenium complex relative to the modified electrode coated only with poly-S is estimated to be 4.5×10$^{-9}$ mol cm$^{-2}$. This provides a crude estimation of the apparent number of layers of the poly (8–11) copolymer.

Step 3: Formation and Properties of Enzyme Layers

Figure 11:
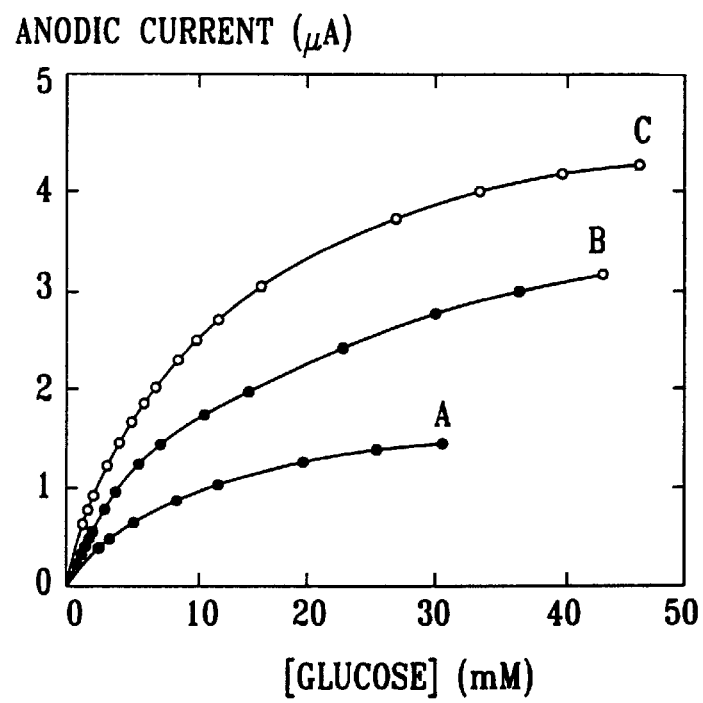
FIG. 11 shows shows the steady-state current-time responses of an electrode coated with an electrically conductive polymer complexed to an enzyme in accordance with a preferred embodiment of the invention as a function of glucose concentration.

Following copolymerization from polymerization solutions containing 0.5 mM 8 and 0.5 mM 11, 30 µL of avidin solution (1 mg mL$^{-1}$) was spread on the poly (8–11) electrode for 20 min. The resulting electrode is carefully washed with phosphate buffer and 30 µL of B-GOD (0.5 mg mL$^{-1}$) were spread on its surface for 20 min at 5° C. The resulting enzyme electrodes were thoroughly rinsed in distilled water and incubated 30 min in stirred phosphate buffer containing 10 mM glucose at 20° C. before use. The same procedure was used for the functionalization of poly 8 film by B-GOD molecules. FIG. 11 depicts the amperometric response of the biosensor as a function of glucose concentration. The sensitivity of the biosensor and its detection limit were determined to be 0.79 mA M$^{-1}$ cm$^{-2}$ and 40 µM respectively.

The modification of poly (8–11) electrodes by a monolayer, 2-layers and 3-layers of B-GOD was obtained by successive elaboration of a B-GOD monolayer following the preceding procedure. A calibration curve for glucose was recorded between each monolayer elaboration. The glucose sensitivity was found to increase almost linearly with the number of B-GOD layers: 0.79, 1.65 and 2.16 mA M$^{-1}$ cm$^{-2}$ (0.9994≦r≦0.9997) for monolayer, 2-layers and 3-layers respectively. In addition, as shown in FIG. 11, the same trend is observed for the current response at nearly saturating glucose conditions (30 mM): 1.33, 2.68 and 3.72 mA for monolayer, 2-layers and 3-layers respectively. The $K^{app}_M$ of the biosensors for glucose was determined from a Michaelis-Menten analysis of the glucose calibration curve, and was found to be 11.4 mM, 11.1 mM and 9.7 mM for monolayer, 2-layers and 3-layers respectively.

Four poly(S-1 1) films of different thicknesses were prepared and modified by an enzyme monolayer. The analytical characteristics of these biosensors for the determination of glucose are summarized in Table 2.

TABLE 2

Influence of the poly (1, 2) thickness on the performance of B-GOD-based biosensors

| Electro-polymerization potential scans[a] | $\Gamma_2$[b] (mol cm$^{-2}$) | No. equivalent monolayers[c] | Glucose sensitivity[d] (mA M$^{-1}$ cm$^{-2}$) | Current response for 30 mM glucose (µA) |
|---|---|---|---|---|
| 3 | 3.1 10$^{-9}$ | 39 | 0.79 | 1.19 |
| 4 | 4.5 10$^{-9}$ | 58 | 0.79 | 1.33 |
| 10 | 1.03 10$^{-8}$ | 129 | 0.84 | 1.27 |
| 20 | 1.68 10$^{-8}$ | 211 | 0.31 | 0.55 |

[a]Between −0.5 and 1.5 V.
[b]Apparent surface coverage of 11 determined from the charge under the Ru(II)/(III) oxidative or reductive peak after transfer of the modified electrode into clean electrolyte.
[c]A monolayer of poly 11 film corresponding to 8 × 10$^{-11}$ mol cm$^{-2}$.
[d]Determined as slope of the initial linear part of the calibration plot for glucose (correlation coefficient 0.9992 ≦ r ≦ 0.9998); applied potential 0.6 V vs SCE: air saturated 0.1 M phosphate buffer (pH 7) kept under stirring.

The apparent surface coverage of polymerized 11 was also correlated to a number of equivalent monolayers. A copolymer thickness between 39 and 129 equivalent monolayers was found to leave the biosensor performance unaffected, indicating that the immobilization of B-GOD molecules is restricted to the interface copolymer-solution. A decrease in sensitivity is observed for a thick poly (8–11) film (211 equivalent monolayers), indicating diffusional constraints for the permeation of $H_2O_2$ through the cross-linked structure of the copolymer. Without wishing to be bound by any particular theory, it is believed that the increase of the distance between the enzymatic layer and the electrode surface may facilitate the diffusion of $H_2O_2$ into the bulk solution.

Table 3 summarizes the electropolymerization conditions and the glucose sensitivity of the biosensors made using different compositions of poly(8–11) films.

TABLE 3

Influence of the copolymer composition on the performance of B-GOD-based biosensors

| Polymerization solution[a] | | Glucose sensitivity[b] |
|---|---|---|
| [8] (mM) | [11] (mM) | (mA M$^{-1}$ cm$^{-2}$) |
| 0.33 | 0.67 | 0.81 |
| 0.50 | 0.50 | 0.79 |
| 0.67 | 0.33 | 0.77 |
| 0.87 | 0.13 | 0.36 |

[a]For each ratio, several poly (8–11) films were prepared, $\Gamma_2$ ranging from 1.5 to 8.2 10$^{-9}$ mol cm$^{-2}$.
[b]Highest sensitivity determined from several biosensors exhibiting different copolymer thickness. Applied potential 0.6 V vs SCE: air saturated 0.1 M phosphate buffer (pH 7) kept under stirring.

Following copolymerization from polymerization solutions containing 0.5 mM 8 and 0.5 mM 11, poly(8–11)-Av-AP electrodes were prepared by the deposition of 30 µL of Av-AP solution (1 mg mL$^{-1}$) on the copolymer surface for 20 min at 5° C. The resulting enzyme electrodes were thoroughly rinsed in distilled water. Then, these electrodes were soaked in stirred 0.1 M Tris-HCI buffer (pH 9) for 30 min, in order to remove the non-specifically adsorbed Av-AP molecules.

The phosphohydrolytic activity of the poly (8–11)-Av-AP electrode was evaluated with p-nitrophenylphosphate (NPP) and yielded a value of 51 mU cm$^{-2}$. This corresponds to only about one third of the theoretical maximum coverage of Av-AP on poly(8–11) film. However, the remaining activity of immobilized Av-AP (34%) is markedly higher than those previously reported for biosensors based on enzymes entrapped in conducting polymers, e.g. in Cosnier, Electroanalysis 9 (1997) 894.

Figure 12:
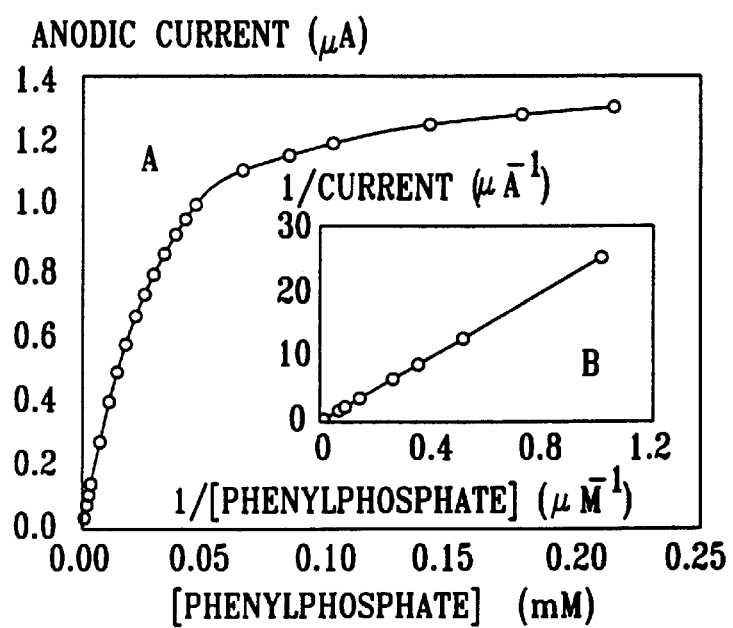
FIG. 12 shows shows the steady-state current-time responses of an electrode coated with an electrically conductive polymer complexed to an enzyme in accordance with a preferred embodiment of the invention as a function of phenylphosphine concentration.

Av-AP catalyzes the hydrolysis of phenyiphosphate into phenol. The amperometric detection of phenylphosphate was assayed in 0.1 M Tris-HCI buffer (pH 9) by holding the poly (8–11)-Av-AP electrode at 0.6 V vs SCE in order to oxidize the enzymically generated phenol. FIG. 12, curve A, presents the amperometric current response of the biosensor as a function of phenylphosphate concentration. The current begins to decrease for increasing phenylphosphate concentrations (up to 2 mM). The sensitivity of the biosensor and its detection limit are 1 mA M$^{-1}$ cm$^{-2}$ and 0.2 µM, respectively. These analytical characteristics are unambiguously better than those recently recorded with a polypyrrole-AP electrode, namely 862 µA M$^{-1}$ cm$^{-2}$ and 20 µM.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An electrically conductive copolymer of the formula I:

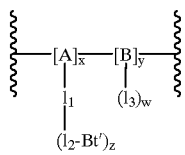

wherein
- A is a first polymerizable monomer which produces an electrically conductive polymer when polymerized, and represents a polymerized unit of said monomer A in the electrically conductive polymer,
- B is a second polymerizable monomer which when copolymerized with monomer A produces an electrically conductive polymer, and represents a polymerized unit of said monomer B in the electrically conductive polymer;
- w is an integer greater than or equal to 0;
- x is an integer greater than or equal to 1;
- y is an integer greater than or equal to 0;
- z is an integer greater than or equal to 1;
- $l_1$ and $l_2$ are each independently covalent linkers or spacer arms;
- $l_3$ is substituent group having a desired chemical functionality; and
- Bt' is selected from the group consisting of biotin and complexes of biotin with a molecule selected from the group consisting of avidin, streptavidin, derivatives of avidin and derivatives of streptavidin,
- wherein said avidin, streptavidin, derivatives of avidin or derivatives of streptavidin may optionally be substituted, and said biotin, whether in free form or in the form of a complex, is covalently bonded to $l_2$.

2. An electrically conductive copolymer according to claim 1, wherein A and B are each independently selected from the group consisting of pyrrole, acetylene, azine, p-phenylene, p-phenylene vinylene, pyrene, thiophene, furan, selenophene, pyridazine, carbazole, aniline, tyramide.

3. A electrically conductive copolymer according to claim 2 wherein A and B are both pyrrole or both carbazole.

4. An electrically conductive copolymer according to claim 1 wherein the ratio of x to y is in the range of about 1:0 to about 1: 1,000,000.

5. An electrically conductive copolymer according to claim 1 wherein $l_1$ and $l_2$ each independently contain functions selected from the group consisting of alkl groups, ether linkages, thioether linkages, carbonyl groups, carbon-carbon double bonds, carbon-carbon triple bonds, amide groups, sulfonamide groups, phosphate groups, thiophosphate groups, ketal groups, ester groups.

6. An electrically conductive polymer according to claim 1, wherein Bt' is a complex of biotin with avidin or an avidin derivative, and said avidin or avidin derivative is substituted by at least one molecule or moiety selected from the group consisting of proteins, peptides, sugars, oligosaccharides, nucleic acids, deoxynucleic acids, metal complexes, lipids, —$NO_2$, and fluorophores.

7. An electrically conductive copolymer according to claim 1, wherein said copolymer is formed on a substrate which is a metallic electrode.

8. An electrically conductive copolymer according to claim 7, wherein said metallic electrode is comprises a metal selected from the group consisting of gold, copper, iron, platinum, palladium, indium, nickel, indium tin oxide, chromium, and silver.

9. An electrically conductive copolymer according to claim 1, wherein said copolymer is formed on a substrate comprising a modified electrode ME, said modified electrode comprising an electrode E and an electrically conductive monolayer M deposited on E, wherein M is a monolayer consisting of monomers B' each covalently bonded via a linker group $l_4$ to a functional group selected from the group consisting of thiol, symmetric disulfide, unsymmetric disulfide, and —$SiX_3$ wherein X is selected from Cl, I, Br, F, and $OR_3$ wherein each R is independently selected from H, $C_1$-$C_6$ alkyl, and aryl, with the proviso that when the functional group to which B' is bonded is $SiX_3$ then electrode E is an indium tin oxide electrode, and when the functional group to which B' is bonded is thiol or disulfide then E is a metallic electrode;
- B' is a monomer B as defined in claim 1; and
- $l_4$ is a linker of 2 to 20 carbons length, optionally including ether linkages, thioether linkages, carbonyl groups, carbon-carbon double bonds, carbon-carbon triple bonds, amide groups, sulfonamide groups, phosphate groups, thiophosphate groups, ketal groups, and ester groups.

10. A process for preparing an electrically conductive copolymer of the general formula I:

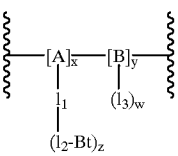

wherein
- A is a first polymerizable monomer which produces an electrically conductive polymer when polymerized, and as shown in formula I represents a polymerized unit of said monomer A in the electrically conductive polymer;
- B is a second polymerizable monomer which when copolymerized with monomer A produces an electrically conductive polymer, and as shown in formula I represents a polymerized unit of said monomer B in the electrically conductive polymer;
- w is an integer greater than or equal to 0;
- x is an integer greater than or equal to 1;
- y is an integer greater than or equal to 0;
- z is an integer greater than or equal to 1;
- $l_1$ and $l_2$ are each independently covalent linkers or spacer arms;
- $l_3$ is substituent group having a desired chemical functionality; and
- Bt is biotin covalently bonded to $l_2$,
- comprising the step of copolymerizing a monomer of the formula II

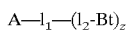

wherein A is a first polymerizable monomer which produces an electrically conductive polymer when polymerized, and $1_1$, $1_2$ and z are as hereinabove defined, with a monomer of the formula III

     III wherein B is a second polymerizable monomer which when copolymerized with monomer A produces an electrically conductive polymer, and $1_3$ and w are as hereinabove defined, on a support, wherein said copolymerizing is effected by electrochemical polymerization or by chemical polymerization.

11. A process for preparing an electrically conductive copolymer according to claim 10, wherein said monomer of formula II is prepared by chemical or enzymatic synthesis.

12. A process for preparing an electrically conductive copolymer according to claim 10, wherein said monomer of formula III is prepared by chemical or enzymatic synthesis.

13. A process for preparing an electrically conductive copolymer according to claim 10, wherein said copolymerization is effected by chemical polymerization using an oxidizing agent.

14. A process according to claim 13 wherein said oxidizing agent is selected from the group consisting of $FeCl_3$, $PbO_2$, $KMnO_4$, $MnO_2$, $CrO_3$, and pyridine complexes.

15. A process according to claim 10, wherein said support is an electrically conductive support.

16. A process according to claim 15, wherein said electrically conductive support is selected from the group of a metal, glass coated by a metal layer and plastic coated by a metal layer.

17. A process according to claim 16 wherein said metal is selected from the group consisting of gold, copper, iron, platinum, palladium, indium, nickel, indium tin oxide, chromium, and silver.

18. A process according to claim 10 further comprising the step of forming a complex between said biotin and a compound selected from the group of avidin, streptavidin, a derivative of avidin and a derivative of streptavidin, after said copolymerizing step, wherein said avidin, streptavidin, derviative of avidin or derivative of streptavidin may optionally be substituted, whereby to form a first film of avidin, streptavidin, avidin derivative or streptavidin derivative.

19. A process according to claim 18, further comprising the steps of:

(a) contacting said first film with biotin whereby to form a second film;

(b) optionally, contacting said second film with a compound selected from avidin, streptavidin, a derivative of avidin and a derivative of streptavidin, whereby to form a third film; and (c) optionally repeating steps (a) and (b) as desired to form a multilayered film on said copolymer of formula I, wherein the outermost layer of said multilayered film may be a layer of avidin, avidin derivative, streptavidin, streptavidin derivative, or biotin.

20. A process according to claim 18, further comprising contacting said first film with biotin substituted with a ligand.

21. A process according to claim 20, wherein said ligand is selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

22. A process according to claim 19, wherein said outermost layer is a layer of avidin, an avidin derivative, streptavidin or a streptavidin derivative, further comprising contacting said outermost layer with biotin or biotin substituted with a ligand.

23. A process according to claim 22, wherein said ligand is selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

24. A process according to claim 20, wherein different areas of said first film are contacted with biotin substituted with different ligands which can function as probes, whereby to form a matrix of probes.

25. A process according to claim 24 wherein said ligands are selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

26. A process according to claim 22, wherein different areas of said outermost layer of said multilayered film are contacted with biotin substituted with different ligands which can function as probes, whereby to form a matrix of probes.

27. A process according to claim 26 wherein said ligands are selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

28. A process according to claim 19, wherein said outermost layer is a layer of biotin, further comprising contacting said outermost layer with a compound selected from avidin substituted with a ligand, a derivative of avidin substituted with a ligand, streptavidin substituted with a ligand and a derivative of streptavidin substituted with a ligand.

29. A process according to claim 28, wherein said ligand is selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

30. A process according to claim 28, wherein different areas of said outermost layer of said multilayered film are contacted with avidin, streptavidin, avidin derivatives or streptavidin derivatives which are substituted with different ligands lo which can function as probes, whereby to form a matrix of probes.

31. A process according to claim 28 wherein said ligands are selected from the group consisting of proteins, peptides, polypeptides, lectins, antibodies, receptors, enzymes, single domain antibodies, monoclonal catalytic antibodies, immunoadhesins, sugars, oligosaccharides, DNA sequences, cDNA sequences, RNA sequences, oligodeoxynucleotides, oligonucleotides, peptide-nucleic acid conjugates, lipids, phospholipids, fluorescent probes, spin labels, metal complexes and polymers or their monomers.

32. A process according to claim 10, wherein A and B are each independently selected from the group consisting of pyrrole, acetylene, azine, p-phenylene, p-phenylene vinylene, pyrene, thiophene, furan, selenophene, pyridazine, carbazole, aniline, tyramide.

33. A process according to claim 10 wherein A and B are both pyrrole or carbazole.

34. A process according to claim 10 wherein the ratio of x to y is in the range of 1:0 to 1: 1,000,000.

35. A process according to claim 10 wherein $l_1$ and $l_2$ each independently contain functions selected from the group consisting of alkyl groups, ether linkages, thioether linkages, carbonyl groups, carbon-carbon double bonds, carbon-carbon triple bonds, amide groups, sulfonamide groups, phosphate groups, thiophosphate groups, ketal groups, and ester groups.

36. A process according to claim 10, wherein said support comprises a modified electrode ME comprising an electrode E and an electrically conductive monolayer M deposited on E, wherein M is a monolayer consisting of monomers B' each covalently bonded via a linker group $l_4$ to a functional group selected from the group consisting of thiol, symmetric disulfide, unsymmetric disulfide, and $SiX_3$ wherein X is selected from Cl, I, Br, F, and $OR_3$ wherein each R is independently selected from H, $C_1$–$C_6$ alkyl, and aryl, with the proviso that when the functional group to which B' is bonded is $SiX_3$ then electrode E is an indium tin oxide electrode, and when the functional group to which B' is bonded is thiol or disulfide then E is a metallic electrode; B' is a monomer B as defined in claim 10;

and $l_4$ is a linker of 2 to 20 carbons length, optionally including ether linkages, thioether linkages, carbonyl groups, carbon-carbon double bonds, carbon-carbon triple bonds, amide groups, sulfonamide groups, phosphate groups, thiophosphate groups, ketal groups, and ester groups.

37. A copolymer according to claim 1, wherein the group A-$l_1$-($l_2$-Bt')$_z$ is selected from the group consisting of:

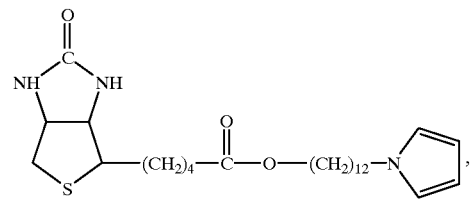

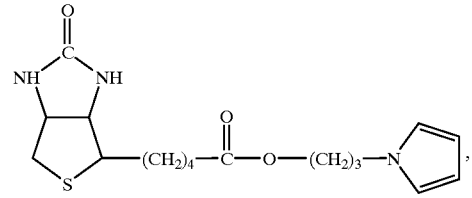

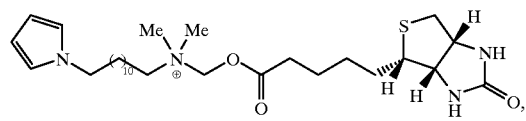

and

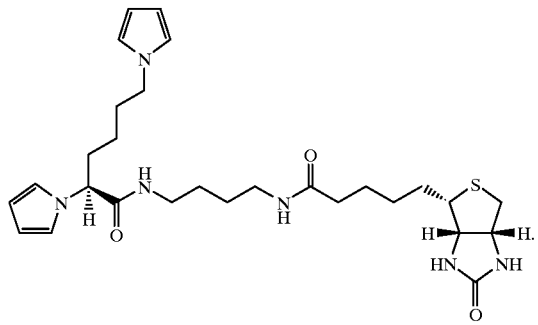

38. A process according to claim 10, wherein said monomer of formula II is selected from the group consisting of:

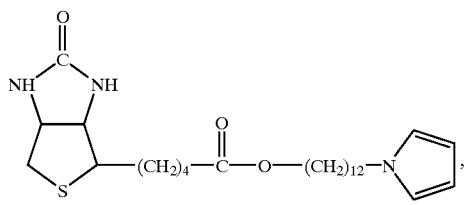

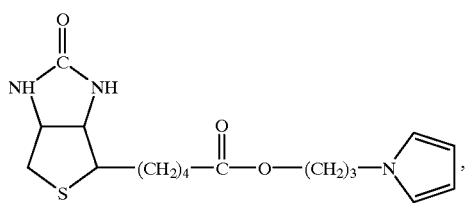

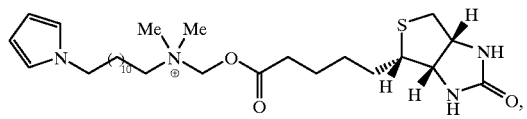

and

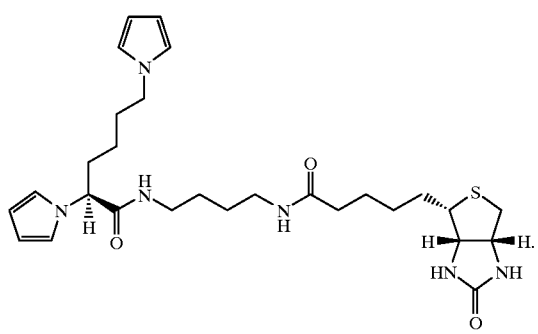

* * * * *